United States Patent
Seth et al.

(10) Patent No.: US 8,501,805 B2
(45) Date of Patent: Aug. 6, 2013

(54) SUBSTITUTED ALPHA-L-BICYCLIC NUCLEOSIDES

(75) Inventors: Punit P. Seth, Carlsbad, CA (US); Eric E. Swayze, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 178 days.

(21) Appl. No.: 13/063,921

(22) PCT Filed: Sep. 23, 2009

(86) PCT No.: PCT/US2009/058013
§ 371 (c)(1),
(2), (4) Date: Mar. 14, 2011

(87) PCT Pub. No.: WO2010/036698
PCT Pub. Date: Apr. 1, 2010

(65) Prior Publication Data
US 2011/0166205 A1 Jul. 7, 2011

Related U.S. Application Data

(60) Provisional application No. 61/099,844, filed on Sep. 24, 2008.

(51) Int. Cl.
*A61K 31/343* (2006.01)
*C07D 307/93* (2006.01)

(52) U.S. Cl.
USPC .......................................... 514/470; 549/463

(58) Field of Classification Search
USPC ................... 514/470; 549/220, 463
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh et al. |
| 4,973,679 A | 11/1990 | Caruthers et al. |
| 4,981,957 A | 1/1991 | Lebleu et al. |
| 5,013,830 A | 5/1991 | Ohtsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |

(Continued)

FOREIGN PATENT DOCUMENTS

| | | |
|---|---|---|
| WO | WO 94/02499 | 2/1994 |
| WO | WO 94/17093 | 8/1994 |
| WO | WO 02/36743 | 5/2002 |
| WO | WO 2005/012371 | 12/2005 |
| WO | WO 2005/012372 | 12/2005 |
| WO | WO 2007/090071 | 8/2007 |
| WO | WO 2007/134181 | 11/2007 |

OTHER PUBLICATIONS

Altschul et al., "Basic Local Alignment Search Tool" J. Mol. Biol. (1990) 215:403-410.

(Continued)

*Primary Examiner* — Taofiq A Solola
(74) *Attorney, Agent, or Firm* — Isis Pharmaceuticals, Inc. Patent Dept.; Casimir Jones

(57) ABSTRACT

The present disclosure describes substituted α-L-bicyclic nucleoside analogs, oligomeric compounds prepared therefrom and methods of using the oligomeric compounds. More particularly, substituted α-L-bicyclic nucleoside analogs are provided, having one or more chiral substituents, that are useful for enhancing properties of oligomeric compounds including binding affinity. In some embodiments, the oligomeric compounds provided herein hybridize to a portion of a target RNA resulting in loss of normal function of the target RNA.

32 Claims, No Drawings

U.S. PATENT DOCUMENTS

| | | | |
|---|---|---|---|
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,426,220 B1 | 7/2002 | Bennett et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 7,053,207 B2 | 5/2006 | Wengel |
| 2003/0082807 A1 | 5/2003 | Wengel |
| 2003/0207841 A1 | 11/2003 | Kaneko et al. |
| 2003/0224377 A1 | 12/2003 | Wengel et al. |
| 2004/0014959 A1 | 1/2004 | Sorensen et al. |
| 2004/0143114 A1 | 7/2004 | Imanishi et al. |
| 2004/0192918 A1 | 9/2004 | Imanishi et al. |
| 2004/0219565 A1 | 11/2004 | Kauppinen et al. |

OTHER PUBLICATIONS

Arzumanov et al., "A Structure-Activity Study of the Inhibition of HIV-1 Tat-Dependent Trans-Activation by Mixmer 2'-O-Methyl Oligoribonucleotides Containing Locked Nucleic Acid (LNA), alpha-L-LNA, or 2'-Thio-LNA Residues" Oligonucleotides (2003) 13:435-453.

Barany et al., "A New Amino Protecting Group Removable by Reduction. Chemistry of the Dithiasuccinoyl (Dts) Function" J. Am. Chem. Soc. (1977) 99:7363-7365.

Barany et al., "Kinetics and Mechanisms of the Thiolytic Removal of the Dithiasuccinoyl (Dts) Amino Protecting Group" J. Am. Chem. Soc. (1980) 102:3084-3095.

Bass, "Double-stranded RNA as a template for gene silencing" Cell (2000) 101:235-238.

Beaucage et al., "The Functionalization of Oligonucleotides via Phosphoramidite Derivatives" Tetrahedron (1993) 49:1925-1963.

Beaucage et al., "The Synthesis of Specific Ribonucleotides and Unrelated Phosphorylated Biomolecules by the Phosphoramidite Method" Tetrahedron (1993) 49:10441-10488.

Beaucage et al., "Advances in the Synthesis of Oligonucleotides by the Phosphoramidite Approach" Tetrahedron (1992) 48:2223-2311.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Fire et al., "Potent and Specific Genetic Interference by Double-Stranded RNA in Caenorhabditis Elegans" Nature (1998) 391:806-811.

Fluiter et al., "On the in vitro and in vivo Properties of Four Locked Nucleic Acid Nucleotides Incorporated into an Anti-H-Ras Antisense Oligonucleotides" ChemBioChem (2005) 6:1104-1109.

Frieden et al., "Expanding the design horizon of antisense oligonucleotides with alpha-L-LNA" Nucleic Acids Res. (2003) 31(21):6365-6372.

Fuchs et al., "Identification of Differentially Expressed Genes by Mutually Subtracted RNA Fingerprinting" Anal. Biochem. (2000) 286:91-98.

Gait et al., "Application of chemically synthesized RNA" RNA: Protein Interactions (1998) 1-36.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Gaubert et al., Nucleosides Nucleotides & Nucleic Acids (2003) 22:1155-1157.

Going et al., "Molecular Pathology and Future Developments" Eur. J. Cancer (1999) 35:1895-1904.

Jungblut et al., "Proteomics in human disease: Cancer, heart and infections diseases" Electrophoresis (1999) 20:2100-2110.

Jurecic et al., "Long-distance DD-PCR and cDNA microarrays" Curr. Opin. Microbiol. (2000) 3:316-321.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Kumar et al., "Synthesis and Hybridization Studies of 2'-Amino-alpha-L-LNA and Tetracyclic "Locked LNA"" J. Org. Chem. (2006) 71:4188-4201.

Larson et al., "Rapid DNA Fingerprinting of Pathogens by Flow Cytometry" Cytometry (2000) 41:203- 208.

Larsson et al., "High-throughput protein expression of cDNA products as a tool in functional genomics" J. Biotech. (2000) 80:143-157.

Madden et al., "Serial analysis of gene expression: from gene discovery to target identification" DDT (2000) 5:415-425.

Medgaard et al., "3'-C-Branched LNA-Type Nucleosides Locked in an N-Type Furanose Ring Conformation: Synthesis, Incorporation into Oligodeoxynucleotides and Hybridization Studies" Journal of Organic Chemistry (2004) 69(19):6311.

Miura et al., "Fluorometric determination of total mRNA with oligo(dT) immobilized on microtiter plates" Clin. Chem. (1996) 42(11):1758-1764.

Montgomery et al., "RNA as a target of double-stranded RNA-mediated genetic interference in Caenorhabditis elegans" Proc Natl. Acad. Sci. (1998) 95:15502-7.

Nishikura, "A Short Primer on RNAi: RNA-Directed RNA Polymerase Acts as a Key Catalyst" Cell (2001) 107:415-418.

Petersen et al., "Alpha-L-LNA (Alpha-I-ribo Configured Locked Nucleic Acid) Recognition of RNA. A Study by NMR Spectroscopy and Molecular Dynamics Simulations" J. Am. Chem. Soc. (2001) 123:74317432.

Prashar et al., "READS: A Method for Display of 3'-End Fragment of Restriction Enzyme-Digested cDNAs for Analysis of Differential Gene Expression" Methods Enzymol. (1999) 303:258-272.

Rajwanshi et al., "The Eight Stereoisomers of LNA (Locked Nucleic Acid): A Remarkable Family of Strong RNA Binding Molecules" Angew Chem Int. Ed. Engl. (2000) 39:1656-1659.

Rajwanshi et al., "LNA stereoisomers: xylo-LNA (Beta-D-xylo configured locked nucleic acid) and Alpha-L-LNA (Alpha-L-ribo configured locked nucleic acid)" J. Chem. Commun. (1999) 1395:1396.

Scaringe, "RNA Oligonucleotide Synthesis via 5'-Sily1-2'-Orthoester Chemistry" Methods (2001) 23:206-217.

Sharma et al., "Synthesis of 3'-and 6'-functonalized locked nucleic acid (LNA) analogs" Nucleic Acids Symposium Series (2008) 52(1):135-136.

Singh et al., "Synthesis of 2'-amino-LNA: A novel conformationally restricted high-affinity oligonucleotide analogue with a handle" J. Org. Chem. (1998) 63: 10035-10039.

Singh et al., "LNA (locked nucleic acids): synthesis and high-affinity nucleic acid recognition" Chem. Commun. (1998) 455-456.

Sorensen et al., "Alpha-L-ribo-Configured Locked Nucleic Acid (Alpha-L-LNA): Synthesis and Properties" J. Am. Chem. Soc. (2002) 124:2164-2176.

Sutcliffe et al., "TOGA: An automated parsing technology for analyzing expression of nearly all genes" PNAS (2000) 97:1976-1981.

Tabara et al., "RNAi in C. elegans: Soaking in the Genome Sequence" Science (1998) 282:430-431.

Tijsterman et al., "RNA hellcase MUT-14-dependent gene silencing triggered in C. elegans by short antisense RNAs" Science (2002) 295:694-7.

Timmons et al., "Specific Interference by Ingested dsRNA" Nature (1998) 395:854.

Timmons et al., "Ingestion of bacterially expressed dsRNAs can produce specific and potent genetic interference in Caenorhabditis Elegans" Gene (2001) 263:103-112.

To, "Identification of Differential Gene Expression by High Throughput Analysis" Comb. Chem. High Throughput Screen (2000) 3:235-241.

Tuschl et al., "Targeted mRNA degradation by double-stranded RNA in vitro" Genes Dev. (1999) 13:3191-7.

Wahlestedt et al., "Potent and nontoxic antisense oligonucleotide containing locked nucleic acids" Proc. Natl. Acad. Sci. USA (2000) 97: 5633-5638.

Zhang et al., "PowerBLAST: A New Network BLAST Application for Interactive or Automated Sequence Analysis and Annotation" Genome Res. (1997) 7:649-656.

International Search Report for application PCT/US2009/058013 dated Mar. 4, 2010.

SUBSTITUTED ALPHA-L-BICYCLIC NUCLEOSIDES

CROSS REFERENCED TO RELATED APPLICATIONS

This application is a U.S. National Phase filing under 35 U.S.C. 371 claiming priority to International Serial No. PCT/US2009/058013 filed Sep. 23, 2009, which claims priority under 35 USC 119(e) to U.S. Provisional Ser. No. 61/099,844, filed Sep. 24, 2008, each of which is incorporated herein by reference in its entirety.

FIELD OF THE INVENTION

Provided herein are substituted α-L-bicyclic nucleosides, oligomeric compounds prepared therefrom and methods of using the oligomeric compounds. More particularly, the substituted α-L-bicyclic nucleosides each have a substituted α-L-bicyclic ribosyl ring replacing the naturally occurring pentofuranose ring. In certain embodiments, the oligomeric compounds hybridize to a portion of a target RNA resulting in loss of normal function of the target RNA.

SEQUENCE LISTING

The present application is being filed along with a Sequence Listing in electronic format. The Sequence Listing is provided as a file entitled CHEM0053USASEQ.txt, created on Mar. 14, 2011 which is 8 Kb in size. The information in the electronic format of the sequence listing is incorporated herein by reference in its entirety.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example affinity and nuclease resistance. One such group of chemically modified nucleosides includes substituted α-L-bicyclic nucleoside wherein the furanose ring is replaced with a bicyclic furanose core having at least one further substituent.

Various bicyclic nucleic acids (BNA) have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

BNAs have also been reported in the scientific literature having the L configuration (α-L-BNA or α-L-LNA) wherein most of these α-L-BNA's have been studied in oligomeric compounds, see for example: Gaubert, G. et al., *Nucleosides Nucleotides Nucleic Acids* 2003, 22, 1155-1157; Kumar et al., *J. Org. Chem.* 2006, 71, 4188-4201; Fluiter et al., *Chem Bio Chem*, 2005, 6, 1-6; Arzumanov et al., *Oligonucleotides*, 2003, 13, 435-453; Frieden et al. *Nucleic Acids Res.*, 2003, 31(21), 6365-6372; Sorensen et al., *J. Am. Chem. Soc.* 2002, 124, 2164-2176; Petersen et al., *J. Am. Chem. Soc.* 2001, 123, 7431-7432; Rajwanshi et al., *Angew Chem Int Ed Engl* 2000, 39, 1656-1659; Rajwanshi et al., *J. Chem. Commun.* 1999, 1395-1396; and U.S. Pat. No. 7,053,207; the text of each is incorporated by reference herein, in their entirety.

Consequently, there remains a long-felt need for agents that specifically regulate gene expression via antisense mechanisms. Disclosed herein are substituted α-L-bicyclic nucleosides that are useful in the preparation of antisense compounds for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are substituted α-L-bicyclic nucleosides, oligomeric compounds comprising the substituted α-L-bicyclic nucleoside and methods of using the oligomeric compounds. The substituted α-L-bicyclic nucleosides impart enhanced properties to oligomeric compounds they are incorporated into.

The variables are defined individually in further detail herein. It is to be understood that the substituted α-L-bicyclic nucleosides, oligomeric compounds comprising these substituted α-L-bicyclic nucleosides, and methods of use thereof provided herein include all combinations of the embodiments disclosed and variables defined herein.

In certain embodiments, provided herein are bicyclic nucleosides having Formula I:

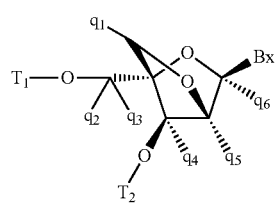

I wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$q_1$, $q_2$, $q_3$, $q_4$, $q_5$ and $q_6$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and
wherein at least one of $q_1$, $q_2$, $q_3$, $q_4$, $q_5$ and $q_6$ is other than H.

In certain embodiments, at least one of $q_1$, $q_2$, $q_3$, $q_4$, $q_5$ and $q_6$ is $C_1$-$C_6$ alkyl or substituted $C_1$-$C_6$ alkyl. In certain embodiments, at least one of $q_1$, $q_2$, $q_3$, $q_4$, $q_5$ and $q_6$ is substituted $C_1$-$C_6$ alkyl. In certain embodiments, each substituted $C_1$-$C_6$ alkyl comprises at least one substituent group selected from halogen, $OJ_1$, $NJ_1J_2$ and CN, wherein each $J_1$ and $J_2$ is, independently, H or $C_1$-$C_6$ alkyl. In certain embodiments, at least one of $q_1$, $q_2$, $q_3$, $q_4$, $q_5$ and $q_6$ is substituted $C_1$-$C_6$ alkyl comprising at least one substituent group selected from fluoro and $OCH_3$.

In certain embodiments, at least one of $q_1$, $q_2$, $q_3$, $q_4$, $q_5$ and $q_6$ is $C_1$-$C_6$ alkyl. In certain embodiments, at least one of $q_1$, $q_2$, $q_3$, $q_4$, $q_5$ and $q_6$ is methyl. In certain embodiments, $q_1$ is methyl.

In certain embodiments, provided herein are bicyclic nucleosides having Formula II:

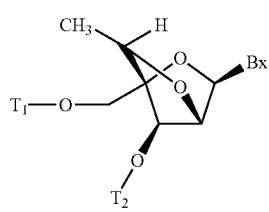

II wherein:
Bx is a heterocyclic base moiety; and
one of $T_1$ and $T_2$ is H or a hydroxyl protecting group and the other of $T_1$ and $T_2$ is H, a hydroxyl protecting group or a reactive phosphorus group.

In certain embodiments, bicyclic nucleosides are provided having Formula I wherein one of $q_2$ and $q_3$ is methyl.

In certain embodiments, bicyclic nucleosides are provided having Formula III:

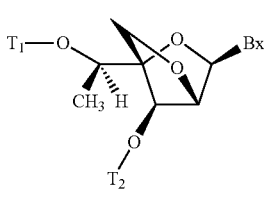

III wherein:
Bx is a heterocyclic base moiety; and
one of $T_1$ and $T_2$ is H or a hydroxyl protecting group and the other of $T_1$ and $T_2$ is H, a hydroxyl protecting group or a reactive phosphorus group.

In certain embodiments, bicyclic nucleosides are provided having Formula IV:

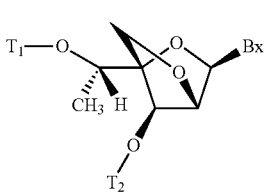

IV wherein:
Bx is a heterocyclic base moiety; and
one of $T_1$ and $T_2$ is H or a hydroxyl protecting group and the other of $T_1$ and $T_2$ is H, a hydroxyl protecting group or a reactive phosphorus group.

In certain embodiments, bicyclic nucleosides are provided having Formula IX:

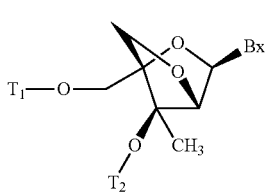

IX wherein:
Bx is a heterocyclic base moiety; and
one of $T_1$ and $T_2$ is H or a hydroxyl protecting group and the other of $T_1$ and $T_2$ is H, a hydroxyl protecting group or a reactive phosphorus group.

In certain embodiments, each of the hydroxyl protecting groups is, independently, selected from benzyl, benzoyl, 2,6-dichlorobenzyl, t-butyldimethylsilyl, t-butyldiphenylsilyl, mesylate, tosylate, dimethoxytrityl (DMT), 9-phenylxanthine-9-yl (Pixyl) and 9-(p-methoxyphenyl)xanthine-9-yl (MOX).

In certain embodiments, $T_1$ is selected from acetyl, benzyl, t-butyldimethylsilyl, t-butyl-diphenylsilyl and dimethoxytrityl. In certain embodiments, $T_1$ is 4,4'-dimethoxytrityl. In certain embodiments, $T_2$ is a reactive phosphorus group. In certain embodiments, the reactive phosphorus group is diisopropylcyanoethoxy phosphoramidite or H-phosphonate. In certain embodiments, $T_1$ is 4,4'-dimethoxytrityl and $T_2$ is diisopropylcyanoethoxy phosphoramidite.

In certain embodiments, provided herein are oligomeric compounds that comprise at least one bicyclic nucleoside having Formula V:

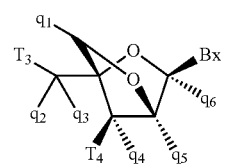

V wherein independently for each bicyclic nucleoside having Formula V:
Bx is a heterocyclic base moiety;
$T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound;
$q_1$, $q_2$, $q_3$, $q_4$, $q_5$ and $q_6$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and
wherein at least one of $q_1$, $q_2$, $q_3$, $q_4$, $q_5$ and $q_6$ is other than H.

In certain embodiments, at least one of $q_1$, $q_2$, $q_3$, $q_4$, $q_5$ and $q_6$ is $C_1$-$C_6$ alkyl or substituted $C_1$-$C_6$ alkyl for each of said at least one bicyclic nucleoside of Formula V. In certain embodiments, at least one of $q_1$, $q_2$, $q_3$, $q_4$, $q_5$ and $q_6$ is substituted $C_1$-$C_6$ alkyl for each of said at least one bicyclic nucleoside of Formula V. In certain embodiments, each substituted $C_1$-$C_6$ alkyl comprises at least one substituent group selected from halogen, $OJ_1$, $NJ_1J_2$ and CN, wherein each $J_1$ and $J_2$ is, independently, H or $C_1$-$C_6$ alkyl. In certain embodiments, each substituted $C_1$-$C_6$ alkyl comprises at least one substituent group selected from fluoro and $OCH_3$.

In certain embodiments, at least one of $q_1$, $q_2$, $q_3$, $q_4$, $q_5$ and $q_6$ is $C_1$-$C_6$ alkyl for each of said at least one bicyclic nucleoside of Formula V. In certain embodiments, at least one of $q_1$, $q_2$, $q_3$, $q_4$, $q_5$ and $q_6$ is methyl for each of said at least one bicyclic nucleoside of Formula V. In certain embodiments, $q_1$ is methyl for each of said at least one bicyclic nucleoside of Formula V.

In certain embodiments, oligomeric compounds are provided having at least one bicyclic nucleoside having Formula V wherein each bicyclic nucleoside having Formula V has the configuration of Formula VI:

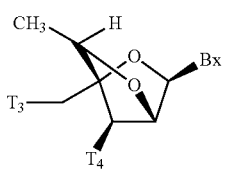

VI wherein:
Bx is a heterocyclic base moiety; and
$T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside having Formula V wherein one of $q_2$ and $q_3$ is methyl for each of said at least one bicyclic nucleoside of Formula V.

In certain embodiments, oligomeric compounds are provided having at least one bicyclic nucleoside having Formula V wherein each bicyclic nucleoside having Formula V has the configuration of Formula VII:

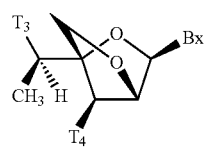

VII wherein:
Bx is a heterocyclic base moiety; and
$T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside having Formula V wherein each bicyclic nucleoside having Formula V has the configuration of Formula VIII:

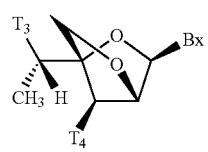

VIII wherein:
Bx is a heterocyclic base moiety; and
$T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside having Formula V wherein each bicyclic nucleoside having Formula V has the configuration of Formula X:

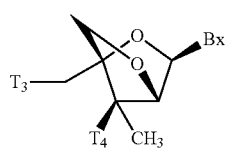

X wherein:
Bx is a heterocyclic base moiety; and
$T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside having Formula V wherein one of $q_4$, $q_5$ or $q_6$ is methyl for each of said at least one bicyclic nucleoside of Formula V.

In certain embodiments, oligomeric compounds are provided having at least one bicyclic nucleoside having Formula V wherein each internucleoside linking group is, independently, selected from phosphodiester or phosphorothioate. In certain embodiments, each internucleoside linking group is a phosphorothioate.

In certain embodiments, oligomeric compounds are provided comprising at least one region of at least two contiguous bicyclic nucleosides having Formula V. In certain embodiments, oligomeric compounds are provided comprising at least two regions of at least two contiguous bicyclic nucleosides having Formula V. In certain embodiments, oligomeric compounds are provided having a gapped motif comprising at least two regions of at least two contiguous bicyclic nucleosides having Formula V. In certain embodiments, oligomeric compounds are provided comprising at least two regions of at least two contiguous bicyclic nucleosides having Formula V and from about 8 to about 14 or from about 9 to about 12 contiguous β-D-2'-deoxyribofuranosyl nucleosides. In certain embodiments, oligomeric compounds are provided having a gapped motif comprising at least two regions of at least two contiguous bicyclic nucleosides having Formula V and from about 8 to about 14 or from about 9 to about 12 contiguous β-D-2'-deoxyribofuranosyl nucleosides.

In certain embodiments, oligomeric compounds are provided comprising one region of from 2 to three contiguous bicyclic nucleosides having Formula V, an optional second region of 1 or 2 contiguous bicyclic nucleosides having Formula V and a third region of from 8 to 14 β-D-2'-deoxyribofuranosyl nucleosides wherein the third region is located between the first and the second regions.

In certain embodiments, oligomeric compounds are provided comprising from about 8 to about 40 monomer subunits. In certain embodiments, oligomeric compounds are provided comprising from about 8 to about 20 monomer subunits. In certain embodiments, oligomeric compounds are provided comprising from about 10 to about 16 monomer subunits. In certain embodiments, oligomeric compounds are provided comprising from about 10 to about 14 monomer subunits.

In certain embodiments, oligomeric compounds are provided wherein $q_1$, $q_2$, $q_3$, $q_4$, $q_5$ and $q_6$ are uniformly modified for each of said at least one bicyclic nucleoside having Formula V. In certain embodiments, oligomeric compounds have a plurality of uniformly modified bicyclic nucleoside having Formula V.

In certain embodiments, methods are provided comprising contacting a cell in an animal with at least one of the oligomeric compounds provided herein. In certain embodiments, the cell is in a human. In certain embodiments, the oligomeric compound is complementary to a target RNA. In certain embodiments, the target RNA is selected from mRNA, pre-mRNA and micro RNA. In certain embodiments, the target RNA is mRNA. In certain embodiments, the target RNA is human mRNA. In certain embodiments, the target RNA is cleaved thereby inhibiting its function.

In certain embodiments, the methods further comprise evaluating the activity of the oligomeric compound on the cell. In certain embodiments, the evaluation comprises detecting the levels of target RNA. In certain embodiments, the evaluation comprises detecting the levels of a protein. In certain embodiments, the evaluation comprises detection of one or more phenotypic effects.

In certain embodiments, oligomeric compounds are provided for use in therapy. In certain embodiments, the therapy involves treating a disease characterized by undesired gene expression. In certain embodiments, the therapy involves treating a disease by inhibiting gene expression.

In certain embodiments, a cell in an animal is to be contacted with at least one of the oligomeric compounds provided herein.

In certain embodiments, oligomeric compounds are provided for the manufacture of a medicament for the treatment of a disease characterized by undesired gene expression.

In certain embodiments, oligomeric compounds are provided for use in the manufacture of a medicament for treating a disease by inhibiting gene expression.

In certain embodiments, a pharmaceutical composition comprising at least one oligomeric compound provided herein and a pharmaceutically acceptable carrier is provided.

DETAILED DESCRIPTION OF THE INVENTION

Provided herein are substituted α-L-bicyclic nucleosides, oligomeric compounds that include such bicyclic nucleosides and methods of using the oligomeric compounds. Also included are intermediates and methods for preparing the substituted α-L-bicyclic nucleosides and incorporating them into oligomeric compounds. More particularly, each of the substituted α-L-bicyclic nucleosides comprise a furanose ring with a 2'-O—CH$_2$-4' bridge and further including at least one substituent group. The heterocyclic base moiety of each of the substituted α-L-bicyclic nucleosides can be optionally substituted with groups to enhance one or more properties such as affinity for a target strand.

Provided herein are substituted α-L-bicyclic nucleosides. As used herein the term "substituted α-L-bicyclic nucleoside" is meant to include bicyclic nucleosides having the general Formula Ia:

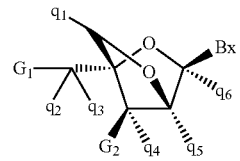

wherein independently for each of the substituted α-L-bicyclic nucleosides:

Bx is a heterocyclic base moiety;

as a monomer, one of G$_1$ and G$_2$ is hydroxyl or protected hydroxyl and the other of G$_1$ and G$_2$ is hydroxyl, a protected hydroxyl or a reactive phosphorus group, when incorporated into an oligomeric compound each G$_1$ and G$_2$, is, independently, hydroxyl, a protected hydroxyl, a linked conjugate group or an internucleoside linking group attaching the bicyclic nucleoside to the oligomeric compound wherein at least one of G$_1$ and G$_2$ is an internucleoside linking group attaching the bicyclic nucleoside to the oligomeric compound;

$q_1$, $q_2$, $q_3$, $q_4$, $q_5$ and $q_6$ are each, independently, H, C$_1$-C$_6$ alkyl, C$_2$-C$_6$ alkenyl, C$_2$-C$_6$ alkynyl, substituted C$_1$-C$_6$ alkyl, substituted C$_2$-C$_6$ alkenyl or substituted C$_2$-C$_6$ alkynyl;

wherein each of the substituted groups, is, independently, mono or poly substituted with optionally protected substituent groups independently selected from halogen, oxo, OJ$_1$, NJ$_1$J$_2$, SJ$_1$, N$_3$, OC(=O)J$_1$ and CN, wherein each J$_1$ and J$_2$ is, independently, H or C$_1$-C$_6$ alkyl; and wherein at least one of $q_1$, $q_2$, $q_3$, $q_4$, $q_5$ and $q_6$ is other than H.

In certain embodiments, oligomeric compounds are provided having at least one bicyclic nucleoside of Formula VI:

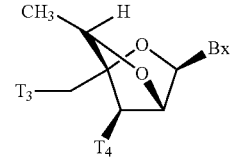

wherein:

Bx is a heterocyclic base moiety; and

T$_3$ and T$_4$ are each, independently, hydroxyl, a protected hydroxyl, a linked conjugate group or an internucleoside linking group attaching the bicyclic nucleoside to the oligomeric compound wherein at least one of T$_3$ and T$_4$ is an internucleoside linking group attaching the bicyclic nucleoside to the oligomeric compound.

In certain embodiments, oligomeric compounds are provided having at least one bicyclic nucleoside of Formula VII:

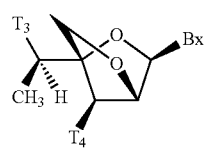

wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside of Formula VIII:

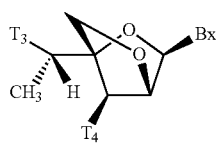

wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside of Formula X:

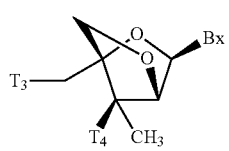

wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside of Formula Va:

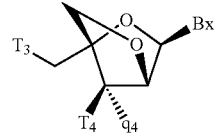

wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside of Formula Vb:

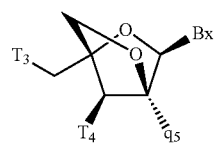

wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In certain embodiments, oligomeric compounds are provided having at least one bicyclic nucleoside of Formula Vc:

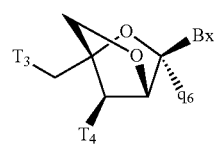

wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

In addition to having good activity in an in vivo assay (Example 16) substituted α-L-bicyclic nucleosides also enhance desired properties of oligomeric compounds in which they are incorporated such as affinity. Oligomeric compounds comprising such substituted α-L-bicyclic nucleosides are also expected to be useful as primers and probes in various diagnostic applications. In certain embodiments, oligomeric compounds comprising at least one of the substituted α-L-bicyclic nucleosides provided herein are expected to be useful as aptamers which are oligomeric compounds capable of binding to aberrant proteins in an in vivo setting.

In certain embodiments, the substituted α-L-bicyclic nucleosides provided herein are useful for modifying oligomeric compounds at one or more positions. Such modified oligomeric compounds can be described as having a particular motif. In certain embodiments, the motifs include without limitation, a gapped motif, a hemimer motif, a blockmer motif, a fully modified motif, a positionally modified motif and an alternating motif. In conjunction with these motifs a wide variety of internucleoside linkages can also be used including but not limited to phosphodiester and phosphorothioate internucleoside linkages which can be incorporated uniformly or in combinations. The positioning of the substituted α-L-bicyclic nucleosides provided herein and the use of linkage strategies can be easily optimized to enhance activity for a selected target. Such motifs can be further modified by the inclusion of a 5' and/or 3'-terminal group such as a conjugate group.

The term "motif" refers to the relative positioning of monomeric subunits within an oligomeric compound. The motif of an oligomeric compound is defined by the pattern created from the positioning of monomeric subunits having one type of sugar group relative to the positioning of monomeric subunits having a different type of sugar group within an oligomeric compound. Only the differences in the sugar groups (which may include sugar surrogate groups as opposed to a more traditional furanose based sugar group) are used to determine the motif Illustrative examples of some different types of sugar groups include without limitation β-D-ribose, β-D-2'-deoxyribose, 2'-substituted sugars (such as 2'-methoxyethoxy), 4'-S-sugars (such as ribose, 2'-deoxyribose and 2'-substituted ribose) and bicyclic modified sugars such as the substituted α-L-bicyclic nucleosides provided herein. The type of heterocyclic base and internucleoside linkage used at each position is variable and is not a factor in determining the motif The presence of one or more other groups including but not limited to capping groups and conjugate groups is also not a factor in determining the motif.

Representative U.S. patents that teach the preparation of representative motifs include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a contiguous sequence of nucleosides comprising two different monomer subunits that alternate for essentially the entire sequence of the oligomeric compound. The pattern of alternation can be described by the formula: 5'-A(-L-B-L-A)$_n$(-L-B)$_{nn}$-3' where A and B are monomeric subunits that have different sugar groups, each L is an internucleoside linking group, nn is 0 or 1 and n is from about 4 to about 12. This permits alternating oligomeric compounds from about 9 to about 26 monomer subunits in length. This length range is not meant to be limiting as longer and shorter oligomeric compounds are also amenable to the present invention. This formula also allows for even and odd lengths for alternating oligomeric compounds. In certain embodiments, the sugar group of one of A or B is selected from β-D-ribose, β-D-2'-deoxyribose, 2'-substituted sugars (such as 2'-methoxyethoxy), 4'-S-sugars (such as ribose, 2'-deoxyribose and 2'-substituted ribose), bicyclic modified sugars (such as a 4'-CH$_2$O-2'bridged nucleoside) and any other sugar modified monomer subunit and the sugar group of the other one of A or B is an α-L-bicyclic nucleoside as provided herein.

As used herein the term "fully modified motif" refers to a contiguous sequence of monomer subunits that each have the same type of sugar group. In certain embodiments, the fully modified motif includes a contiguous sequence of substituted α-L-bicyclic nucleosides. In certain embodiments, the 3' and 5'-terminal ends comprise unmodified nucleosides.

As used herein the term "hemimer motif" refers to an oligomeric compound comprising a contiguous sequence of monomer subunits wherein each of the monomers subunits have the same sugar group except for an additional contiguous sequence which has a different type of sugar group and is located at the 5' or 3'-terminus of the oligomeric compound. In general a hemimer normally comprises a short contiguous sequence of monomer subunits (1, 2, 3, 4 or about 5) having the same type of sugar group located at one of the termini with a longer contiguous sequence of monomer subunits having a different type of sugar group making up the rest of the oligomeric compound. In certain embodiments, the hemimer motif comprises a contiguous sequence of from about 10 to about 28 monomer subunits of one type with from 1 to 5 or from 2 to 5 monomer subunits of a second type located at one of the termini. In certain embodiments the hemimer is a contiguous sequence of from about 8 to about 20 β-D-2'-deoxyribonucleosides having from 1-12 contiguous substituted α-L-bicyclic nucleosides located at one of the termini. In certain embodiments the hemimer is a contiguous sequence of from about 8 to about 20 β-D-2'-deoxyribonucleosides having from 1-5 contiguous substituted α-L-bicyclic nucleosides located at one of the termini. In certain embodiments the hemimer is a contiguous sequence of from about 12 to about 18 β-D-2'-deoxyribonucleosides having from 1-3 contiguous substituted α-L-bicyclic nucleosides located at one of the termini.

As used herein the term "blockmer motif" refers to an oligomeric compound comprising a contiguous sequence of monomer subunits wherein the sugar groups of each monomer subunit is the same except for an internal block of contiguous monomer subunits having a different type of sugar group. A blockmer overlaps somewhat with a gapmer in the definition but typically only the monomer subunits in the block have modified sugar groups in a blockmer and only the monomer subunits in the external regions have modified sugar groups in a gapmer with the remainder of monomer subunits in the blockmer or gapmer being β-D-2'-deoxyribonucleosides or β-D-ribonucleosides. In certain embodiments, blockmers can have other types of modified monomer subunits throughout the oligomeric compound at positions not occupied by the block.

As used herein the term "positionally modified motif" refers to a sequence of monomer subunits having one type of sugar group that is interrupted with two or more regions of from 1 to about 5 contiguous monomer subunits having another type of sugar group. In certain embodiments, each of the two or more regions may have the same or different sugar group, e.g. each region is uniformly modified but the uniform modification can be different between the regions. In certain embodiments, a positionally modified oligomeric compound is a sequence of from 8 to 20 β-D-2'-deoxyribonucleosides that further includes two or three regions of from 2 to about 5 contiguous substituted α-L-bicyclic nucleosides each. Positionally modified oligomeric compounds are distinguished from gapped motifs, hemimer motifs, blockmer motifs and alternating motifs because the pattern of regional substitution defined by any positional motif is not defined by these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein sugar group of each monomer subunit within a particular region is the same. When the sugar groups of the external regions are the same the gapmer is a symmetric gapmer and when the sugar groups of the external regions are different from each other the gapmer is an asymmetric gapmer. In certain embodiments, the external regions are small (1, 2, 3, 4 or about 5 monomer subunits) and the monomer subunits comprise non-naturally occurring sugar and/or sugar surrogate groups and the internal region comprises β-D-2'-deoxyribonucleosides. In certain embodiments, the external regions each, independently, comprise from 1 to about 5 monomer subunits having non-naturally occurring sugar groups and/or sugar surrogate groups and the internal region comprises from 6 to 18 unmodified monomer subunits which are routinely unmodified nucleosides. The internal region or the gap generally comprises β-D-2'-deoxyribonucleosides but can be a sequence of sugar modified nucleosides. The types of nucleosides that are generally used to differentiate the regions of a gapped oligomeric compound include without limitation β-D-ribose, β-D-2'-deoxyribose, 2'-substituted sugars (such as 2'-methoxyethoxy), 4'-S-sugars (such as 4'-S-ribose, 4'-S-2'-deoxyribose and 4'-S-2'-substituted ribose), bicyclic modified sugars (such as the α-L-bicyclic nucleosides provided herein) and sugar surrogates (such as morpholino).

In certain embodiments, the gapped oligomeric compounds comprise an internal region of β-D-2'-deoxyribonucleosides with one of the external regions comprising substituted α-L-bicyclic nucleosides as disclosed herein. In certain embodiments, the gapped oligomeric compounds comprise an internal region of β-D-2'-deoxyribonucleosides with both of the external regions comprising substituted α-L-bicyclic nucleosides as disclosed herein. In certain embodiments, the gapped oligomeric compounds comprise an internal region of β-D-2'-deoxyribonucleosides with both of the external regions comprising substituted α-L-bicyclic nucleosides selected from Formula VI, VII, VIII, Va, Vb or Vc. One gapped oligomeric compound comprising substituted α-L-bicyclic nucleosides was used in an in vivo assay as illustrated in Example 16. The oligomeric compound comprising 14 nucleosides with 2 substituted α-L-bicyclic nucleosides positioned at each of the 3' and 5' ends with 10 unmodified β-D-2'-deoxyribonucleosides in the internal region e.g. a 2/10/2 gapmer.

In certain embodiments, gapped oligomeric compounds are provided comprising one or two substituted α-L-bicyclic nucleosides at the 5'-end, two or three substituted α-L-bicyclic nucleosides at the 3'-end and an internal region of from 10 to 16 β-D-2'-deoxyribonucleosides. In certain embodiments, gapped oligomeric compounds are provided comprising one substituted α-L-bicyclic nucleoside at the 5'-end, two substituted α-L-bicyclic nucleosides at the 3'-end and an internal region of from 10 to 16 β-D-2'-deoxyribonucleosides. In certain embodiments, gapped oligomeric compounds are provided comprising one substituted α-L-bicyclic nucleoside at the 5'-end, two substituted α-L-bicyclic nucleosides at the 3'-end and an internal region of from 10 to 14 β-D-2'-deoxyribonucleosides. In certain embodiments, the internal region includes monomer subunits alone or in combination with β-D-2'-deoxyribonucleosides. In certain embodiments, oligomeric compounds are provided that include, but are not limited to, one or more 5' or 3'-terminal groups such as further modified or unmodified nucleosides, linked conjugate groups and other groups known to the art skilled.

In certain embodiments, gapped oligomeric compounds are provided that are from about 10 to about 21 nucleosides in length. In certain embodiments, gapped oligomeric compounds are provided that are from about 12 to about 16 nucleosides in length. In certain embodiments, gapped oligomeric compounds are provided that are from about 12 to about 14 nucleosides in length.

The terms "substituent" and "substituent group," as used herein, are meant to include groups that are typically added to other groups or parent compounds to enhance desired properties or give desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound. Such groups include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic, heteroaryl, heteroarylalkyl, amino (—$NR_{bb}R_{cc}$), imino(=$NR_{bb}$), amido (—C(O)$NR_{bb}R_{cc}$ or —N($R_{bb}$)C(O)$R_{aa}$), azido (—$N_3$), nitro (—$NO_2$), cyano (—CN), carbamido (—OC(O)$NR_{bb}R_{cc}$ or —N($R_{bb}$)C(O)O$R_{aa}$), ureido (—N($R_{bb}$)C(O)$NR_{bb}R_{cc}$), thioureido (—N($R_{bb}$)C(S)$NR_{bb}R_{cc}$), guanidinyl (—N($R_{bb}$)C(=$NR_{bb}$)$NR_{bb}R_{cc}$), amidinyl (—C(=$NR_{bb}$)$NR_{bb}R_{cc}$ or —N($R_{bb}$)C($NR_{bb}$)$R_{aa}$), thiol (—$SR_{bb}$), sulfinyl (—S(O)$R_{bb}$), sulfonyl (—S(O)$_2R_{bb}$), sulfonamidyl (—S(O)$_2NR_{bb}R_{cc}$ or —N($R_{bb}$)S(O)$_2R_{bb}$) and conjugate groups. Wherein each $R_{aa}$, $R_{bb}$ and $R_{cc}$ is, independently, H, an optionally linked chemical functional group or a further substituent group with a preferred list including, without limitation H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The term "alkyl," as used herein, refers to a saturated straight or branched hydrocarbon radical containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include, but are not limited to, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, but are not limited to, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" or "alicyclyl" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted alkyl radical. This term is meant to include $C_1$-$C_{12}$ alkyl groups having an amino substituent at any position and wherein the alkyl group attaches the aminoalkyl group to the parent molecule. The alkyl and/or amino portions of the aminoalkyl group can be further substituted with substituent groups.

The terms "aralkyl" and "arylalkyl," as used herein, refer to a radical formed between an alkyl group and an aryl group wherein the alkyl group is used to attach the aralkyl group to a parent molecule. Examples include, but are not limited to, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include, but are not limited to, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined having an alky radical is used to attach the heteroarylalkyl group to a parent molecule. Examples include, but are not limited to, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include, [1,3] dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes groups comprising C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems that are single or polycyclic wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that are uniform or have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. In certain embodiments, mono or poly cyclic structures can be attached to a parent molecule directly through a ring atom, through a substituent group or a bifunctional linking moiety.

The term "oxo" refers to the group (=O).

The terms "bicyclic nucleic acid (BNA)" and "bicyclic nucleoside" refer to a nucleoside wherein the furanose portion of the nucleoside includes a bridge connecting two carbon atoms on the furanose ring, thereby forming a bicyclic ring system. The substituted α-L-bicyclic nucleosides provided herein are a species of the genus of bicyclic nucleosides.

The terms "stable compound" and "stable structure" are meant to indicate a compound that is sufficiently robust to survive isolation to a useful degree of purity from a reaction mixture, and formulation into an efficacious therapeutic agent. Only stable compounds are contemplated herein.

Linking groups or bifunctional linking moieties such as those known in the art are useful for attachment of chemical functional groups, conjugate groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as a chemical functional group or a conjugate group. In some embodiments, the linker comprises a chain structure or an oligomer of repeating units such as ethylene glycols or amino acid units. Examples of functional groups that are routinely used in bifunctional linking moieties include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, oligomeric compounds are modified by covalent attachment of one or more 5' or 3'-terminal groups. The term "terminal group" as used herein is meant to include useful groups known to the art skilled that can be placed on one or both of the 3' and 5'-ends of an oligomeric compound for various purposes such as enabling the tracking of the oligomeric compound (a fluorescent label or other reporter group), improving the pharmacokinetics or pharmacodynamics of the oligomeric compound (a group for enhancing uptake and delivery) or enhancing one or more other desirable properties of the oligomeric compound (group for improving nuclease stability or binding affinity). In certain embodiments, 3' and 5'-terminal groups include without limitation, one or more modified or unmodified nucleosides, conjugate groups, capping groups, phosphate moieties and protecting groups.

In certain embodiments, oligomeric compounds are modified by covalent attachment of one or more conjugate groups. In general, conjugate groups modify one or more properties of the attached oligomeric compound including but not limited to pharmakodynamic, pharmacokinetic, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene and Wuts, Protective Groups in Organic Synthesis, 3rd edition, John Wiley & Sons, New York (1999).

Groups can be selectively incorporated into oligomeric compounds of the invention as precursors. For example an amino group can be placed into a compound of the invention as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal, et al., Protocols for Oligonucleotide Conjugates, Eds, Humana Press; New Jersey, 1994; Vol. 26 pp. 1-72.

Examples of hydroxyl protecting groups include, but are not limited to, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Where more preferred hydroxyl protecting groups include, but are not limited to, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl) xanthine-9-yl (MOX).

Examples of amino protecting groups include, but are not limited to, carbamate-protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include, but are not limited to, triphenylmethyl (trityl), benzyl (Bn), and the like.

In certain embodiments, oligomeric compounds are prepared by connecting nucleosides with optionally protected phosphorus containing internucleoside linkages. Representative protecting groups for phosphorus containing internucleoside linkages such as phosphodiester and phosphoro-thioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage, S. L. and Iyer, R. P., Tetrahedron, 49 No. 10, pp. 1925-1963 (1993); Beaucage, S. L. and Iyer, R. P., Tetrahedron, 49 No. 46, pp. 10441-10488 (1993); Beaucage, S. L. and Iyer, R. P., Tetrahedron, 48 No. 12,pp. 2223-2311 (1992).

The term "orthogonally protected" refers to functional groups which are protected with different classes of protecting groups, wherein each class of protecting group can be removed in any order and in the presence of all other classes (see, Barany, G. and Merrifield, R. B., *J. Am. Chem. Soc.*, 1977, 99, 7363; idem, 1980, 102, 3084.) Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

In certain embodiments, compounds having reactive phosphorus groups are provided that are useful for forming internucleoside linkages including for example phosphodiester and phosphoro-thioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. A preferred synthetic solid phase synthesis utilizes phosphoramidites ($P^{III}$ chemistry) as reactive phosphites. The intermediate phosphite compounds are subsequently oxidized to the $P^V$ state using known methods to yield, phosphodiester or phosphorothioate internucleotide linkages. Additional reactive phosphates and phosphites are disclosed in Tetrahedron Report Number 309 (Beaucage and Iyer, Tetrahedron, 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, non-phosphorus containing internucleoside linking groups such as formacetyl and methyleneimino, and neutral non-ionic internucleoside linking groups such as amide-3 (3'-CH$_2$—C(=O)—N(H)-5'), amide-4 (3'-CH$_2$—N(H)—C(=O)-5').

In certain embodiments, oligomeric compounds are provided containing modified e.g. non-naturally occurring internucleoside linkages. Two main classes of internucleoside linkages are defined by the presence or absence of a phosphorus atom. Modified internucleoside linkages having a phosphorus atom include, but are not limited to, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050,certain of which are commonly owned with this application, and each of which is herein incorporated by reference.

In certain embodiments, oligomeric compounds are provided having one or more internucleoside linkages that don't contain a phosphorus atom. Such oligomeric compounds include, but are not limited to, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. In the context of this invention, the term "oligonucleoside" refers to a sequence of two or more nucleosides that are joined by internucleoside linkages that do not have phosphorus atoms.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

As used herein the phrase "neutral internucleoside linkage" is intended to include internucleoside linkages that are non-ionic. Neutral internucleoside linkages include but are not limited to phosphotriesters, methylphosphonates, MMI (3'-CH$_2$—N(CH$_3$)—O-5'), amide-3 (3'-CH$_2$—C(=O)—N (H)-5'), amide-4 (3'-CH$_2$—N(H)—C(=O)-5'), formacetal (3'-O—CH$_2$—O-5'), and thioformacetal (3'-S-CH$_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook Eds. ACS Symposium Series 580; Chapters 3 and 4, (pp. 40-65)). Further neutral internucleoside linkages include nonionic linkages comprising mixed N, O, S and CH$_2$ component parts.

The compounds described herein can be prepared by any of the applicable techniques of organic synthesis, as, for example, illustrated in the examples below. Many such techniques are well known in the art. However, many of the known techniques are elaborated in *Compendium of Organic Synthetic Methods* (John Wiley & Sons, New York) Vol. 1, Ian T. Harrison and Shuyen Harrison (1971); Vol. 2, Ian T. Harrison and Shuyen Harrison (1974); Vol. 3, Louis S. Hegedus and Leroy Wade (1977); Vol. 4, Leroy G. Wade Jr., (1980); Vol. 5, Leroy G. Wade Jr. (1984); and Vol. 6, Michael B. Smith; as well as March, J., *Advanced Organic Chemistry*, 3rd Edition, John Wiley & Sons, New York (1985); *Comprehensive Organic Synthesis. Selectivity, Strategy & Efficiency in Modern Organic Chemistry, In 9 Volumes*, Barry M. Trost, Editor-in-Chief, Pergamon Press, New York (1993); *Advanced Organic Chemistry, Part B: Reactions and Synthesis*, 4th Ed.; Carey and Sundberg; Kluwer Academic/Plenum Publishers: New York (2001); *Advanced Organic Chemistry, Reactions, Mechanisms, and Structure*, 2nd Edition, March, McGraw Hill (1977); *Protecting Groups in Organic Synthesis*, 2nd Edition, Greene, T. W., and Wutz, P. G. M., John Wiley & Sons, New York (1991); and *Comprehensive Organic Transformations*, 2nd Edition, Larock, R. C., John Wiley & Sons, New York (1999).

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)- such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

As used herein the term "oligomeric compound" is meant to include a polymer having at least a region that is capable of hybridizing to a nucleic acid molecule. The term "oligomeric compound" includes oligonucleotides, oligonucleotide analogs and oligonucleosides as well as oligomeric compounds containing one or more nucleotide mimetics and/or mixed polymers comprising nucleic acid and non-nucleic acid components and chimeric oligomeric compounds comprising mixtures of nucleosides from any of these categories.

Oligomeric compounds are routinely prepared linearly but can be joined or otherwise prepared to be circular and may also include branching. Oligomeric compounds can form double stranded constructs such as for example two strands hybridized to form double stranded compositions. The double stranded compositions can be linked or separate and can include overhangs on the ends. In general, an oligomeric compound comprises a backbone of linked monomeric subunits where each linked monomeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified. The linkage-sugar unit, which may or may not include a heterocyclic base, may be substituted with a mimetic such as the monomers in peptide nucleic acids. The ability to modify or substitute portions or entire monomers at each position of an oligomeric compound gives rise to a large number of possible motifs.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

In the context of this invention, the term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and increased stability in the presence of nucleases.

In the context of this invention, the term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include, but are not limited to, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and CH$_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference. The term "nucleobase" or "heterocyclic base moiety" as used herein, is intended to by synonymous with "nucleic acid base or mimetic thereof." In general, a nucleobase or heterocyclic base moiety is any substructure that contains one or more atoms or groups of atoms capable of hydrogen bonding to a base of a nucleic acid.

As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993.

Modified nucleobases include, but are not limited to, universal bases, hydrophobic bases, promiscuous bases, size-expanded bases, and fluorinated bases as defined herein. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

In certain embodiments, oligomeric compounds may also contain one or more nucleosides having modified sugar moieties. The furanosyl sugar ring can be modified in a number of ways including substitution with a substituent group (2', 3', 4' or 5'), bridging to form a BNA and substitution of the 4'-O with a heteroatom such as S or N(R). Some representative U.S. patents that teach the preparation of such modified sugars include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; 5,700,920; 6,600,032 and International Application PCT/US-2005/019219, filed Jun. 2, 2005 and published as WO 2005/121371 on Dec. 22, 2005 certain of which are commonly owned with the instant application, and each of which is herein incorporated by reference in its entirety. A representative list of preferred modified sugars includes but is not limited to substituted sugars having a 2'-F, 2'-OCH$_2$ or a 2'-O(CH$_2$)$_2$—OCH$_3$ (2'-MOE or simply MOE) substituent group; 4'-thio modified sugars, 4'-thio-2'-substituted sugars and bicyclic modified sugars.

As used herein the term "nucleoside mimetic" is intended to include those structures used to replace the sugar or the sugar and the base and not necessarily the linkage at one or more positions of an oligomeric compound such as for example nucleoside mimetics having morpholino or bicyclo [3.1.0]hexyl sugar mimetics e.g. non furanose sugar units with a phosphodiester linkage. The term "sugar surrogate" overlaps with the slightly broader term "nucleoside mimetic" but is intended to indicate replacement of the sugar unit (furanose ring) only. The term "nucleotide mimetic" is intended to include those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

As used herein the term "modified nucleoside" is meant to include all manner of modified nucleosides that can be incorporated into an oligomeric compound using oligomer synthesis. The term includes nucleosides having a ribofuranose sugar and can include a heterocyclic base but abasic modified nucleoside are also envisioned. One group of representative modified nucleosides includes without limitation bicyclic nucleosides, 2'-modified nucleosides, 4'-thio modified nucleosides, 4'-thio-2'-modified nucleosides and base modified nucleosides.

As used herein the term "monomer subunit" is meant to include all manner of monomer units that are amenable to oligomer synthesis with one preferred list including monomer subunits such as β-D-ribonucleosides, β-D-2'-deoxyribnucleosides, 2'-substituted nucleosides, 4'-S-modified nucleosides, (such as 4'-S-ribonucleosides, 4'-S-2'-deoxyribonucleosides and 4'-S-2'-substituted ribonucleosides), bicyclic modified nucleosides (such as the α-L-bicyclic nucleosides provided herein and more generally bicyclic ribonucleosides wherein the ribose sugar group has a 2'-O—CHR$_1$-4' bridging group, wherein R$_1$ is H, alkyl or substituted alkyl), nucleoside mimetics and nucleosides having sugar surrogates (such as morpholino modified mimetics).

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the substituted α-L-bicyclic nucleosides provided herein and may also include other monomer subunits including but not limited to nucleosides, modified nucleosides and nucleoside mimetics. As such the term monomer subunit encompasses all manner of monomer units that are amenable to oligomer synthesis with one preferred list including monomer subunits such as the β-D-ribonucleosides, β-D-2'-deoxyribonucleosides, 2'-substituted nucleosides, 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic ribonucleosides wherein the ribose sugar group has a 2'-O—CHR$_1$-4' bridging group, wherein R$_1$ is H, alkyl or substituted alkyl-including α-L-bicyclic nucleosides as provided herein) and nucleoside mimetics or nucleosides having a sugar surrogate (such as the substituted CeNAs provided herein).

In certain embodiments, oligomeric compounds comprise from about 8 to about 80 monomer subunits in length. One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds comprise from about 10 to 16 monomer subunits in length. One having ordinary skill in the art will appreciate that this embodies oligomeric compounds of 10, 11, 12, 13, 14, 15 or 16 monomer subunits in length, or any range therewithin.

In certain embodiments, oligomeric compounds comprise from about 12 to 16 monomer subunits in length. One having ordinary skill in the art will appreciate that this embodies oligomeric compounds of 12, 13, 14, 15 or 16 monomer subunits in length, or any range therewithin.

In certain embodiments, oligomeric compounds comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds of any of a variety of ranges of lengths of linked monomer subunits are provided. In certain embodiments, oligomeric compounds are provided consisting of X-Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9,-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-29, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, ranges for the length of the oligomeric compounds are 8-16, 8-40, 10-12, 10-14, 10-16, 10-18, 10-20, 10-21, 12-14, 12-16, 12-18, 12-20 and 12-24 linked monomer subunits.

In certain embodiments, the ranges for the oligomeric compounds listed herein are meant to limit the number of monomer subunits in the oligomeric compounds, however such oligomeric compounds may further include protecting groups such as hydroxyl protecting groups, optionally linked conjugate groups, 5' and/or 3'-terminal groups and/or other substituents.

In certain embodiments, oligomerization of modified and unmodified nucleosides and mimetics thereof, is performed according to literature procedures for DNA (Protocols for Oligonucleotides and Analogs, Ed. Agrawal (1993), Humana Press) and/or RNA (Scaringe, Methods (2001), 23, 206-217; Gait et al., Applications of Chemically synthesized RNA in RNA:Protein Interactions, Ed. Smith (1998), 1-36; Gallo et al., Tetrahedron (2001), 57, 5707-5713) synthesis as appropriate. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069.

Commercially available equipment routinely used for the support medium based synthesis of oligomeric compounds and related compounds is sold by several vendors including, for example, Applied Biosystems (Foster City, Calif.). Any other means for such synthesis known in the art may additionally or alternatively be employed. Suitable solid phase techniques, including automated synthesis techniques, are described in F. Eckstein (ed.), Oligonucleotides and Analogues, a Practical Approach, Oxford University Press, New York (1991).

The synthesis of RNA and related analogs relative to the synthesis of DNA and related analogs has been increasing as efforts in RNAi increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]-methyl (2'-O—$CH_2$—O—$Si(iPr)_3$ (TOM), and the 5'-O-silyl ether-2'-ACE (5'-O-bis(trimethylsiloxy)-cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS=5'-O-DMT-2'-O-t-butyldimethylsilyl; TOM=2'-O-[(triisopropylsilyl)oxy]methyl; DOD/ACE=(5'-O-bis(trimethylsiloxy)cyclododecyloxysilyl ether-2'-O-bis (2-acetoxyethoxy)methyl; and FPMP=5'-O-DMT-2'-O-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In the context of this invention, "hybridization" means the pairing of complementary strands of oligomeric compounds. In certain embodiments, one mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid to cause a loss of activity, and there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Complementary," as used herein, refers to the capacity for precise pairing of two nucleobases regardless of where the two are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent.

Suitable target segments may also be combined with their respective complementary antisense oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The oligomeric compounds provided herein can also be applied in the areas of drug discovery and target validation. In certain embodiments, provided here is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound of the invention. These methods can also be performed in parallel or in combination with other experiments to determine the function of unknown genes for the process of target validation or to determine the validity of a particular gene product as a target for treatment or prevention of a particular disease, condition, or phenotype. In certain embodiments, there is provided oligomeric compounds of the invention for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds of the invention may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or therapeutics, can be used as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more oligomeric compounds are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A., 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively.

Example 1

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 2

Oligonucleoside Synthesis

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligonucleotides: Unsubstituted and substituted phosphodiester (P=O) oligonucleotides can be synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation is effected in certain embodiments by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligonucleotides are recovered by precipitating with greater than 3 volumes of ethanol from a 1 M NH$_4$OAc solution. Phosphinate oligonucleotides can be prepared as described in U.S. Pat. No. 5,508,270.

Alkyl phosphonate oligonucleotides can be prepared as described in U.S. Pat. No. 4,469,863.

3'-Deoxy-3'-methylene phosphonate oligonucleotides can be prepared as described in U.S. Pat. Nos. 5,610,289 or 5,625,050.

Phosphoramidite oligonucleotides can be prepared as described in U.S. Pat. Nos. 5,256,775 or 5,366,878.

Alkylphosphonothioate oligonucleotides can be prepared as described in published PCT applications PCT/US94/00902 and PCT/US93/06976 (published as WO 94/17093 and WO 94/02499, respectively).

3'-Deoxy-3'-amino phosphoramidate oligonucleotides can be prepared as described in U.S. Pat. No. 5,476,925.

Phosphotriester oligonucleotides can be prepared as described in U.S. Pat. No. 5,023,243.

Borano phosphate oligonucleotides can be prepared as described in U.S. Pat. Nos. 5,130,302 and 5,177,198.

Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal linked oligonucleosides can be prepared as described in U.S. Pat. Nos. 5,264,562 and 5,264,564.

Ethylene oxide linked oligonucleosides can be prepared as described in U.S. Pat. No. 5,223,618.

Example 3

Oligonucleotide Isolation

After cleavage from the controlled pore glass solid support or other support medium and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32 +/−48). For some studies oligonucleotides are purified by HPLC, as described by Chiang et al., J. Biol. Chem. 1991, 266, 18162-18171. Results obtained with HPLC-purified material are generally similar to those obtained with non-HPLC purified material.

Example 4

Oligonucleotide Synthesis—96 Well Plate Format

Oligonucleotides can be synthesized via solid phase P(III) phosphoramidite chemistry on an automated synthesizer capable of assembling 96 sequences simultaneously in a 96-well format. Phosphodiester internucleotide linkages are afforded by oxidation with aqueous iodine. Phosphorothioate internucleotide linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites are purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides are cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 5

Oligonucleotide Analysis Using 96-Well Plate Format

The concentration of oligonucleotide in each well is assessed by dilution of samples and UV absorption spectroscopy. The full-length integrity of the individual products is evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 6

Cell Culture and Oligonucleotide Treatment

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture is incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Other suitable transfection reagents known in the art include, but are not limited to, CYTOFECTIN™, LIPOFECTAMINE™, OLIGOFECTAMINE™, and FUGENE™. Other suitable transfection methods known in the art include, but are not limited to, electroporation.

Example 7

Real-Time Quantitative PCR Analysis of Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents were obtained from Invitrogen Life Technologies (Carlsbad, Calif.). RT, real-time PCR was carried out by adding 20 µL PCR cocktail (2.5× PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multi-plexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 µL of RIBOGREEN™ working reagent (RIBOGREEN™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 8

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*,Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*,Volume 2, pp. 11.4.1-11.11.5,John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11,John Wiley & Sons, Inc., 1998. Western blot (immunoblot) analysis is standard in the art and can be found at, for example, Ausubel, F. M. et al., *Current Protocols in Molecular Biology*, Volume 2,pp. 10.8.1-10.8.21,John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2,pp. 11.2.1-11.2.22, John Wiley & Sons, Inc., 1991.

Example 9

Design of Phenotypic Assays and in vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Arm Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In vivo Studies

The individual subjects of the in vivo studies described herein are warm-blooded vertebrate animals, which includes humans.

Example 10

RNA Isolation

Poly(A)+mRNA Isolation

Poly(A)+mRNA is isolated according to Miura et al., (Clin. Chem., 1996, 42, 1758-1764). Other methods for poly (A)+mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

```
                                            (SEQ ID NO: 2)
Forward primer: AATGGCTAAGTGAAGATGACAATCAT (SEQ ID NO: 3)
Reverse primer: TGCACATATCATTACACCAGTTCGT
```

And the PCR probe:
FAM-TTGCAGCAATTCACTGTAAAGCTG-GAAAGG-TAMRA (SEQ ID NO: 4), where FAM is the fluorescent dye and TAMRA is the quencher dye.

Example 12

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 µl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 13

Preparation of Compound 11

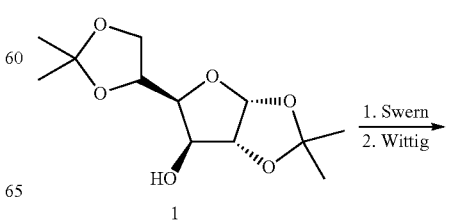

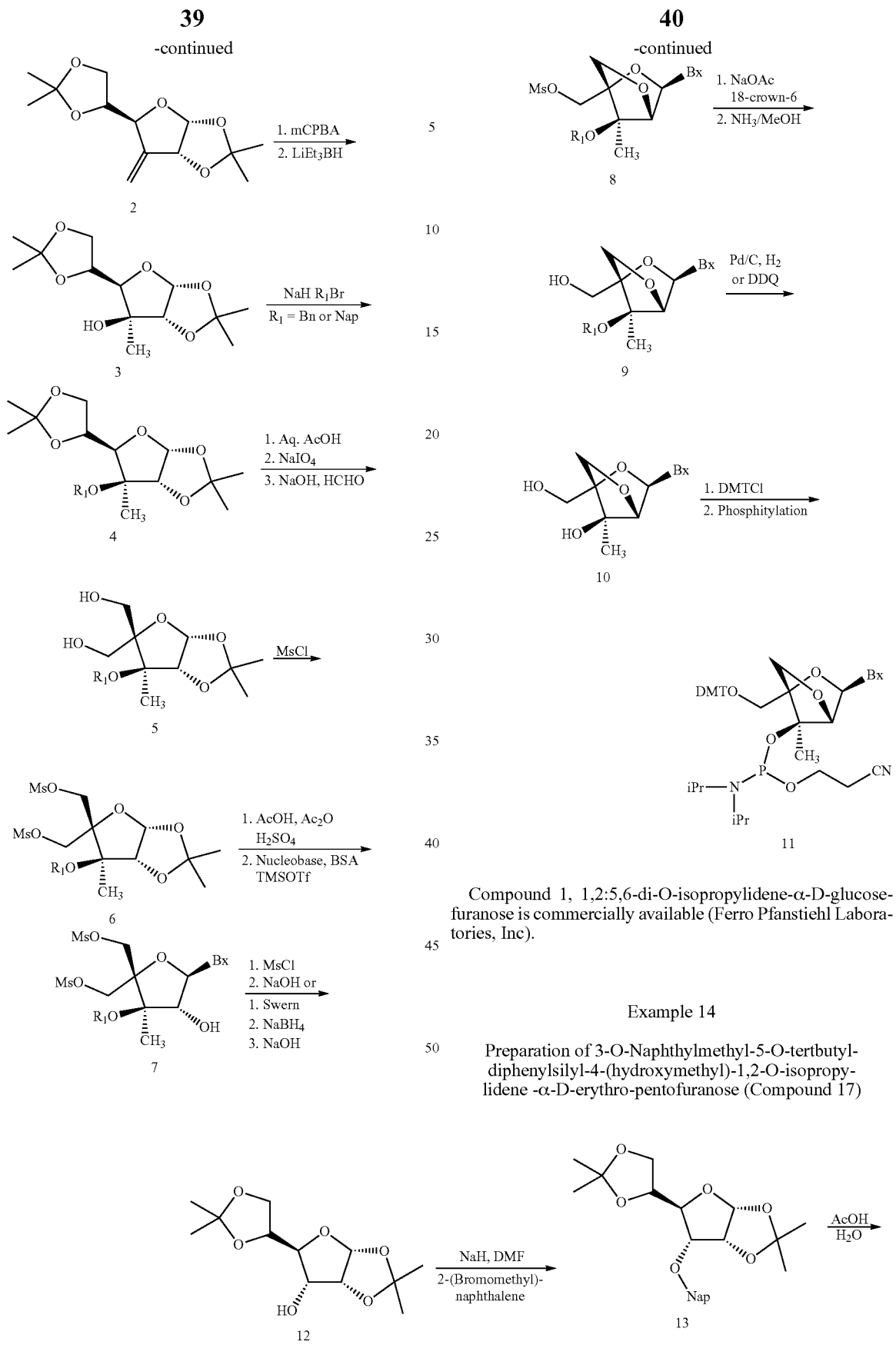
Compound 1, 1,2:5,6-di-O-isopropylidene-α-D-glucose-furanose is commercially available (Ferro Pfanstiehl Laboratories, Inc).
Example 14
Preparation of 3-O-Naphthylmethyl-5-O-tertbutyl-diphenylsilyl-4-(hydroxymethyl)-1,2-O-isopropylidene-α-D-erythro-pentofuranose (Compound 17)

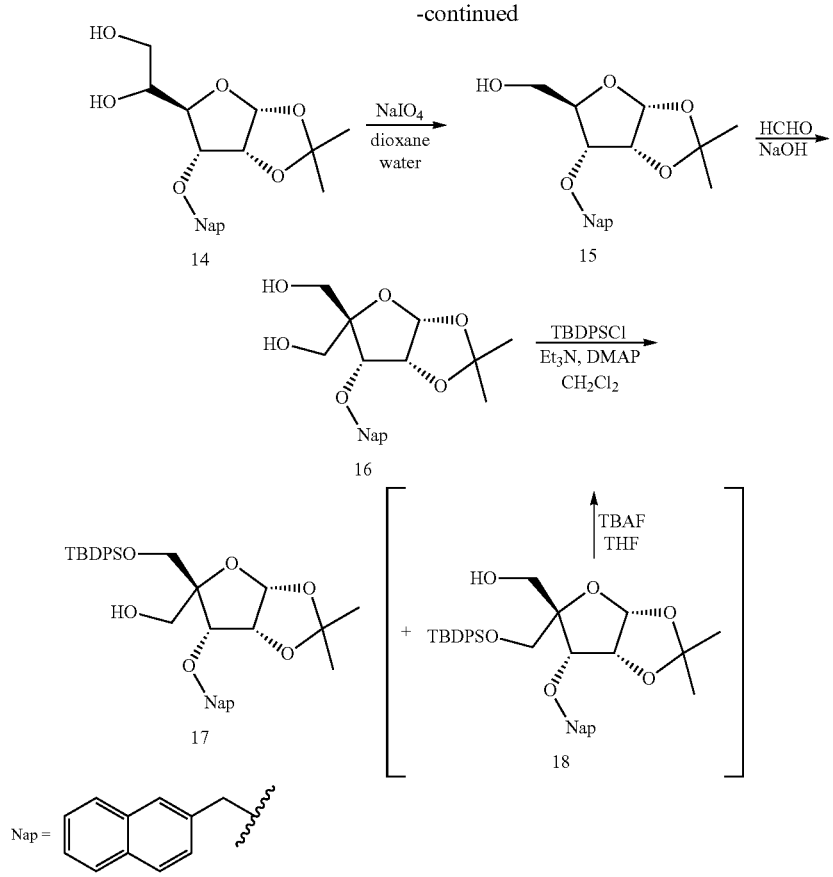

A) Preparation of Compound 13

Commercially available 1,2;5,6-di-O-isopropylidene-α-D-allofuranose (Cole-Parmer), Compound 12, (135 g, 519.0 mmol) and 2-(bromomethyl)-naphthalene (126 g, 570.0 mmol) were dissolved in DMF (500 mL) in a three-necked flask (500 mL) and the reaction was cooled in an ice bath. Sodium hydride (60% w/w, 29 g, 727.0 mmol) was carefully added (6 g portions every 10 minutes) to the reaction with stirring continued for 60 minutes after the addition was complete. TLC showed completion of reaction (starting Compound 12 was consumed). The reaction was carefully poured onto crushed ice (ca. 500 g) and the resulting slurry was stirred vigorously until all the ice melted. A resulting off-white solid was collected by filtration and suspended in water. The suspension was stirred vigorously using a mechanical stirrer for 30 minutes after which the solid was collected by filtration and suspended in hexanes. The suspension was stirred vigorously for 30 minutes after which the solid was collected by filtration and air dried for 4-6 hours and then dried under high vacuum over $P_2O_5$ for 16 hours to provide Compound 13 (206.0 g, 99%) as an off-white solid. $^1$H NMR (300 MHz, CDCl$_3$) δ: 7.85 (m, 4H), 7.48 (m, 3H), 5.74 (s, 1H), 4.92 (d, 1H, J=11.7), 4.75 (d, 1H, J=11.6), 4.58 (m, 1H), 4.36 (m, 1H), 4.15 (m, 1H), 4.03-3.86 (m, 3H), 1.61 (s, 3H), 1.36 (s, 9H).

B) Preparation of Compound 14

Compound 13 (200.0 g, 0.5 moles) was added in small portions to a solution of acetic acid (2.2 L) and water (740 mL). The reaction was stirred at room temperature for 16 h after which, TLC analysis (30% EtOAc/hexanes) indicated complete consumption of Compound 13. The reaction was concentrated under reduced pressure until most of the acetic acid was removed. The remaining solution was poured into a stirred mixture of EtOAc (1 L) and water (1 L). Solid KOH was then added to the above mixture until the aqueous layer was strongly basic (pH>12). The organic layer was then separated, washed with saturated sodium bicarbonate solution and then brine. The washed organic layer was dried (Na$_2$SO$_4$), filtered and concentrated under reduced pressure to provide Compound 14 as a yellow foam which was used without further purification.

C) Preparation of Compound 15

A solution of NaIO$_4$ (107.0 g) in water (3 L) was added over 40 minutes to a stirred (mechanical stirrer) solution of Compound 14 (crude from above) in dioxane (1.5 L). After 60 minutes the reaction mixture was poured into EtOAc (1.5 L) and the organic layer was separated, washed with water (1 L), brine (1 L), dried (Na$_2$SO$_4$) and concentrated to provide Compound 15 as a yellow oil, which was used without any further purification.

D) Preparation of Compound 16

Compound 15 (crude from above) was dissolved in a mixture of THF (500) and water (500 mL) and the reaction was cooled in an ice bath. 2N NaOH (600 mL) and formaldehyde (250 mL of a 37% aqueous solution) were added to the reaction with stirring at room temperature for 3 days. The reaction was then poured into EtOAc (1 L) and washed with water (1 L), brine (1 L) and evaporated under reduced pressure until approximately 200 mL of EtOAc was left (a white precipitate was formed in the process). Hexanes (300 mL) was added to the precipitate and the mixture was allowed to stand for 16 hours after which the white solid was collected by filtration, washed with hexanes and dried under high vacuum over P$_2$O$_5$ to provide Compound 16 as a white solid (124 g, 66% from Compound 13). $^1$H NMR (300 MHz, CDCl$_3$) δ: 7.85 (m, 4H), 7.48 (m, 3H), 5.75 (d, 1H, J=3.9), 4.96 (d, 1H. J=11.8), 4.75 (d, 1H, J=11.8), 4.66 (m, 1H), 4.26 (d, 1H, J=5.2), 3.95 (m, 2H), 3.79 (m, 1H), 3.63 (m, 1H), 2.39 (m, 1H, OH), 1.66 (s, 3H), 1.34 (s, 3H).

E) Preparation of Compounds 17 and 18 tert-Butyldiphenylchlorosilane (305.0 mmol, 84.0 mL) was added to a cold (0° C.) stirring solution of Compound 16 (278.0 mmol, 100.0 g) and triethylamine (305 mmol, 43.0 mL) in dichloromethane (600 mL). After the addition was complete, the reaction was warmed to room temperature stirring was continued for 16 hours. MeOH (50 mL) was added (to quench the excess TBDPSCl) to the reaction and stirring was continued for another 2 hours at room temperature. The reaction was diluted with chloroform and the organic layer was washed with 10% HCl, saturated NaHCO$_3$ and brine. The organic layer was dried (Na$_2$SO$_4$) and concentrated to provide an oil. Hexanes (150 mL) was added to the oil and the mixture was sonicated until a solution resulted. The solution was seeded with a small amount of Compound 17 (previously isolated by column chromatography). After standing for 16 hours additional hexanes was added to the thick slurry and the solid was collected by filtration. The solid was then resuspended in hexanes and stirred vigorously for 30 minutes. The solid was collected by filtration to provide Compound 17 (80.5 g, 48%) after drying under high vacuum for 16 hours. The filtrates were combined and concentrated under reduced pressure. The resulting oil was redissolved in minimum amount of hexanes and passed through a plug of silica gel (eluting with 20% EtOAc in hexanes). Fractions containing the Compound 17 were combined, concentrated and crystallized as described above to provide a second crop of Compound 17 (20 g, 12%) as a white solid. Further elution of the silica gel plug with 50% EtOAc in hexanes provided pure Compound 17 (40.0 g, 24%) as a thick oil. In addition a mixture of 17 and 18 (15 g, 9%) was also isolated as a thick oil. Compound 17; $^1$H NMR (300 MHz, CDCl$_3$) δ: 7.83 (m, 4H), 7.56 (m, 7H), 7.30 (m, 6H), 5.80 (s, 1H), 4.97 (d, 1H, J=11.4), 4.70 (m, 2H), 4.46 (m, 1H), 3.92-3.66 (m, 4H), 2.39 (m, 1H, OH), 1.67 (s, 3H), 1.37 (s, 3H), 0.92 (s, 9H). Compound 18; $^1$H NMR (300 MHz, CDCl$_3$) δ: 7.9-7.3 (m, 17H), 5.71 (d, 1H, J=3.9), 4.86 (d, 1H, J=12.2), 4.74 (d, 1H, J=12.2), 4.56 (m, 1H), 4.22 (d, 1H, J=11.1), 4.18 (m, 1H), 4.07 (d, 1H, J=11.1), 4.02 (dd, 1H, J=4.2, 12.0), 3.64 (dd, 1H, J=9.4, 11.9), 1.89 (m, 1H), 1.25 (s, 6H), 1.05 (s, 9H).

F) Recovery of Compound 16 from Compound 18

Tetrabutylammonium fluoride (70 mL of a 1M solution in THF) was added to a cold (0° C.) stirring solution of Compound 18 (62.7 mmol, 37.5 g) in THF (250 mL) after which, the reaction was allowed to warm to room temperature gradually. After stirring for an additional 72 hours, the reaction was concentrated under vacuum and the residue was poured onto crushed ice. The flask was rinsed with some additional THF (3 times) and added to the above suspension. The supernatant was removed by decantation and the solid at the bottom was added to a stirring mixture of hexanes (200 mL) and water (200 mL). After stirring for 2 hours, the flocculent solid was collected by filtration, washed with additional water and hexanes and dried under high vacuum to provide Compound 16 (20 g, 89%) as a white solid.

Example 15

Preparation of Compound 28

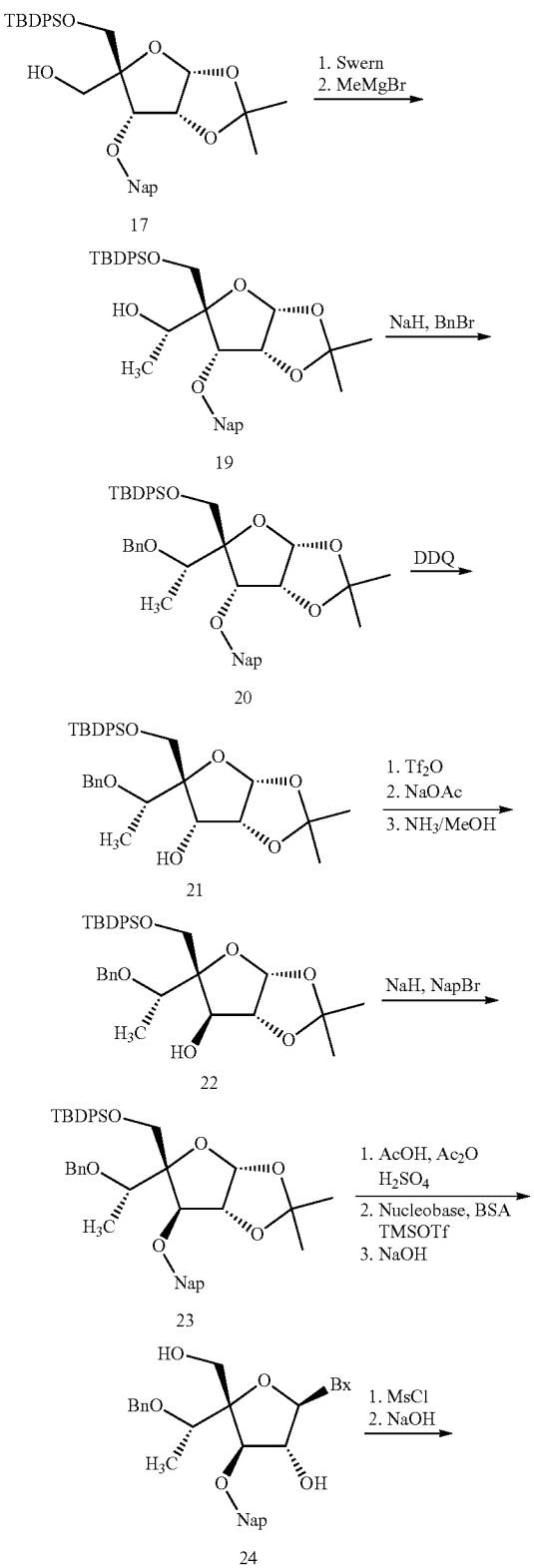

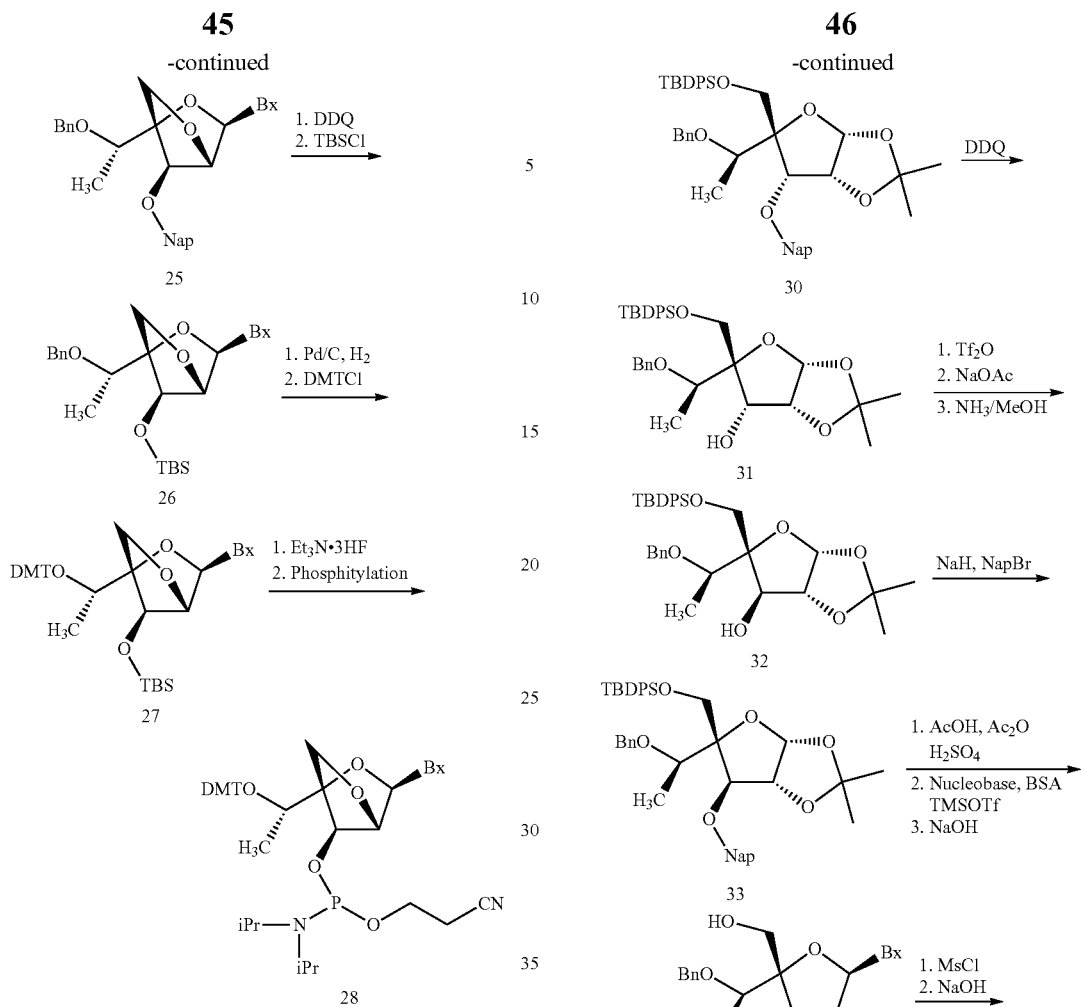
Compound 17 is prepared as per the procedures illustrated in Example 14.
Example 16
Preparation of Compound 38
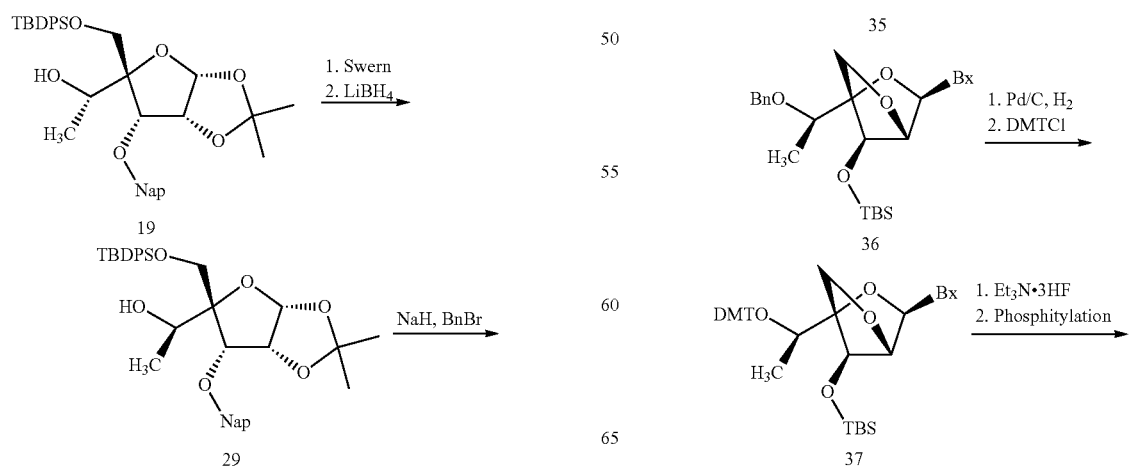

47

-continued

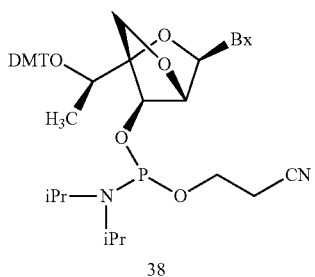

38

Compound 19 is prepared as per the procedures illustrated in Example 15.

Example 17

Preparation of Compound 44

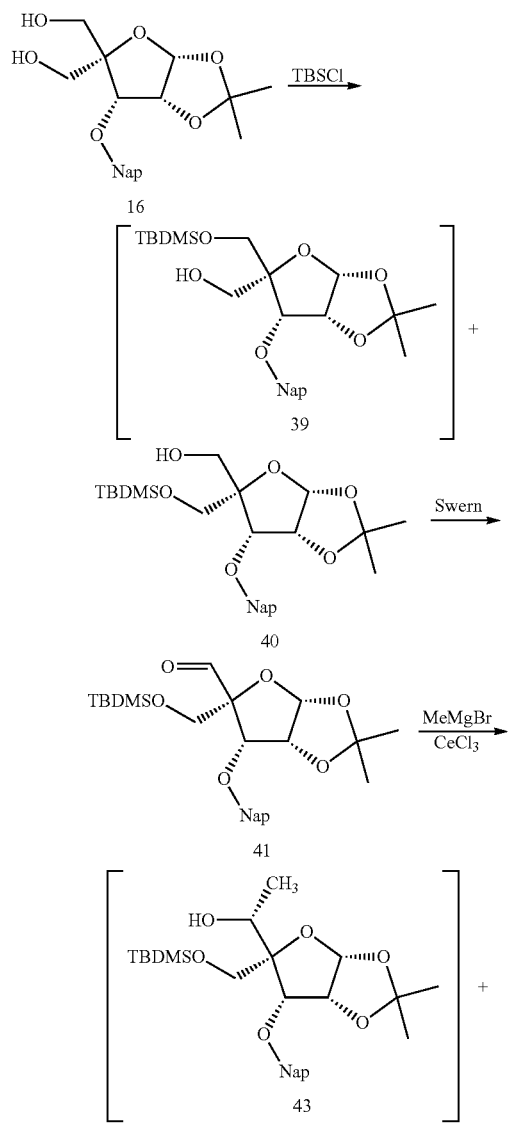

48

-continued

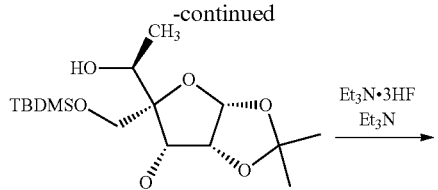

42

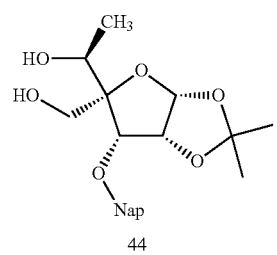

44

A) Preparation of Compound 40

Compound 16 was prepared as per the procedures illustrated in Example 14. A solution of tert-butyldimethylsilyl-chloride (6.24 g, 40.7 mmol) in dichloromethane (10 mL) was added over 10 min, via an addition funnel, to a cold (0° C.) solution of Compound 16 (12 g, 38.8 mmol, prepared according to the procedure of Moffatt et al, *J. Org. Chem.* 1979, 44, 1301), triethylamine (11.44 mL, 81.5 mmol) and 4-dimethylaminoethylpyridine (0.47 g, 3.9 mmol) in $CH_2Cl_2$ (184 mL). After the addition was complete, the reaction was gradually warmed to room temperature and stirred for an additional 16 hours. The reaction was diluted with $CH_2Cl_2$ and sequentially washed with 5% aqueous HCl, saturated $NaHCO_3$, brine, dried ($Na_2SO_4$) and concentrated under vacuum. Purification by column chromatography ($SiO_2$, eluting with 10% EtOAc/hexanes-20% EtOAc/hexanes-30% EtOAc/hexanes) gave Compound 39 (11.53 g, 59%) and Compound 40 (3.93 g, 22%) as white solids.

B) Preparation of Compound 41

Dimethylsulfoxide (1.84 mL, 26.0 mmol) was added to a cold (−78° C.) solution of oxalyl chloride (1.14 mL, 13.0 mmol) in $CH_2Cl_2$ (70 mL). The solution was stirred at −78° C. for 30 minutes and a solution of Compound 40 (3.93 g, 9.3 mmol) in $CH_2Cl_2$ (20 mL) was added via a cannula. The stirring was continued for 45 minutes and triethylamine (5.48 mL, 39.0 mmol) was added to the reaction. The reaction was stirred for an additional 40 minutes after which it was poured into $CH_2Cl_2$ and the organic layer was sequentially washed with 5% aqueous HCl, saturated $NaHCO_3$, brine, dried ($Na_2SO_4$) and concentrated under vacuum to provide Compound 41, which was used without purification in the next step.

C) Preparation of Compound 42 and Compound 43

A suspension of cerium III chloride (4.57 g, 18.6 mmol) in THF (55 mL) was stirred at room temperature for 90 minutes. The reaction was cooled in an ice bath and methyl magnesium bromide (13.3 mL of a 1M solution in THF) was added over 5 minutes and the stirring continued for another 90 minutes. A solution of crude Compound 41 (from above) in THF (15 mL) was added to the reaction. After stirring for another 90 minutes, the reaction was quenched with sat $NH_4Cl$ solution and poured into EtOAc. The organic layer was sequentially washed with 5% aqueous HCl, saturated $NaHCO_3$, brine, dried ($Na_2SO_4$) and concentrated under vacuum. Purification by column chromatography ($SiO_2$, eluting sequentially with CHCl₃; 3% acetone/CHCl₃; and finally 5% acetone/CHCl₃) gave Compound 42 (2.25 g, 55% from Compound 40) and Compound 43 (1.84 g, 45% from Compound 40).

Compound 42 ¹H NMR (300 MHz, CDCl₃) δ: 7.44-7.29 (m, 5H), 5.68 (d, 1H, J=3.8), 4.76 (d, 1H, J=12.0), 4.62 (d, 1H, J=12.0), 4.58 (m, 1H), 4.44 (d, 1H, J=10.3), 4.08 (d, 1H, J=5.3), 3.95 (m, 1H), 3.81 (d, 1H, J=10.3), 2.84 (d, 1H, J=7.5), 1.60 (s, 3H), 1.30 (s, 3H), 1.20 (d, 3H, J=6.4), 0.88 (s, 9H), 0.08 (s, 3H), 0.05 (s, 3H).

Compound 43 ¹H NMR (300 MHz, CDCl₃) δ: 7.39-2.29 (m, 5H), 5.73 (d, 1H, J=3.9), 4.76 (d, 1H, J=11.7), 4.58 (m, 1H, partially overlapped), 4.56 (d, 1H, J=11.7), 4.16 (d, 1H, J=5.2), 4.14-4.04 (m, 3H), 2.43 (d, 1H, J=3.8), 1.62 (s, 3H), 1.32 (s, 3H), 1.17 (d, 3H, J=6.52), 0.88 (s, 9H), 0.08 (s, 3H), 0.05 (s, 3H).

D) Preparation of Compound 44

Triethylamine trihydrofluoride (5.7 mL, 34.8 mmol) was added to a solution of a mixture of Compounds 42 and 43 and triethylamine (2.0 mL, 14.5 mmol) in THF (50 mL). The reaction was stirred at room temperature for 48 h and the solvent was removed on a rotary evaporator. The thick oil was diluted with ethyl acetate and the organic layer was washed with water, brine, dried (Na₂SO₄) and concentrated. Purification by column chromatography (SiO₂, eluting with 20% acetone in dichloromethane) provided Compound 44 (4.2 g) as a white solid.

Example 18

Preparation of Compound 53

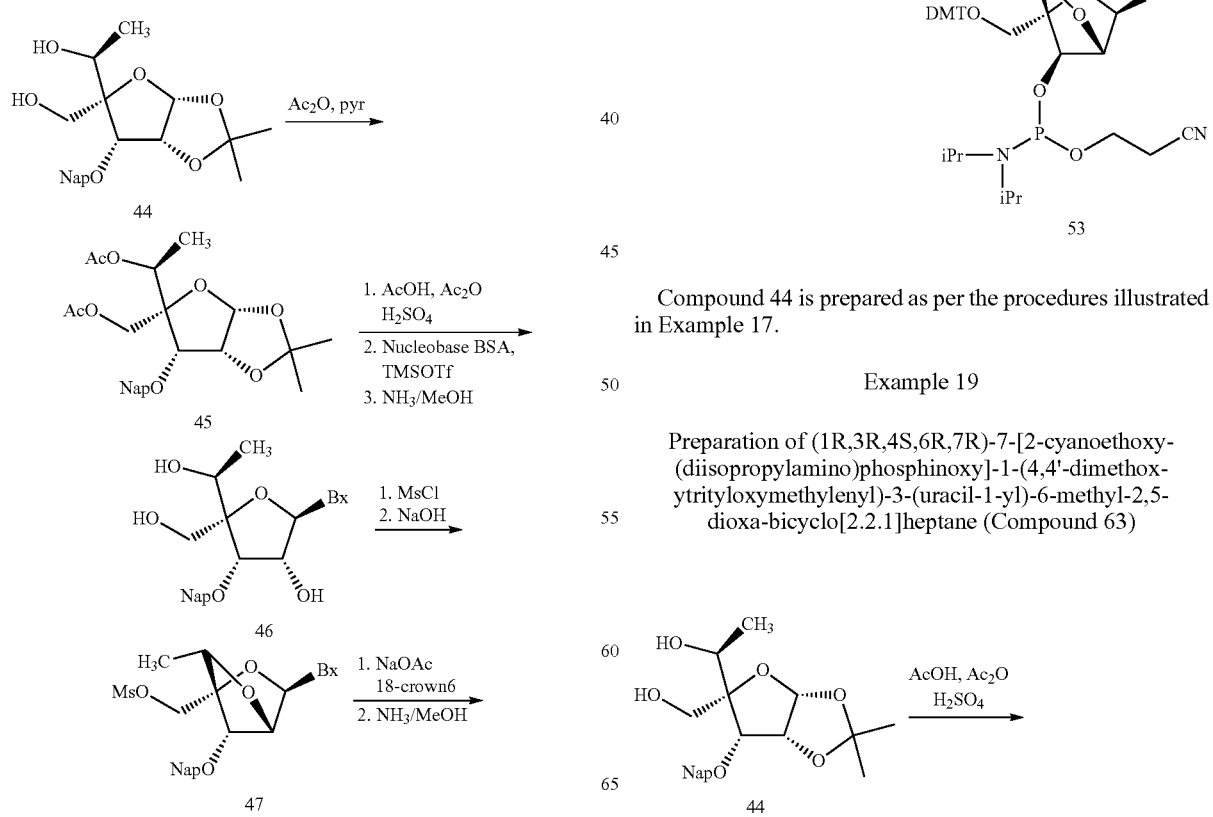

Compound 44 is prepared as per the procedures illustrated in Example 17.

Example 19

Preparation of (1R,3R,4S,6R,7R)-7-[2-cyanoethoxy-(diisopropylamino)phosphinoxy]-1-(4,4'-dimethoxytrityloxymethylenyl)-3-(uracil-1-yl)-6-methyl-2,5-dioxa-bicyclo[2.2.1]heptane (Compound 63)

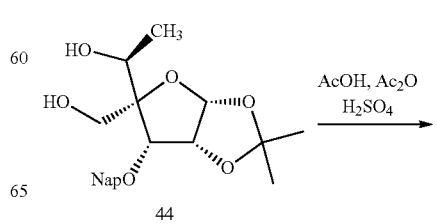

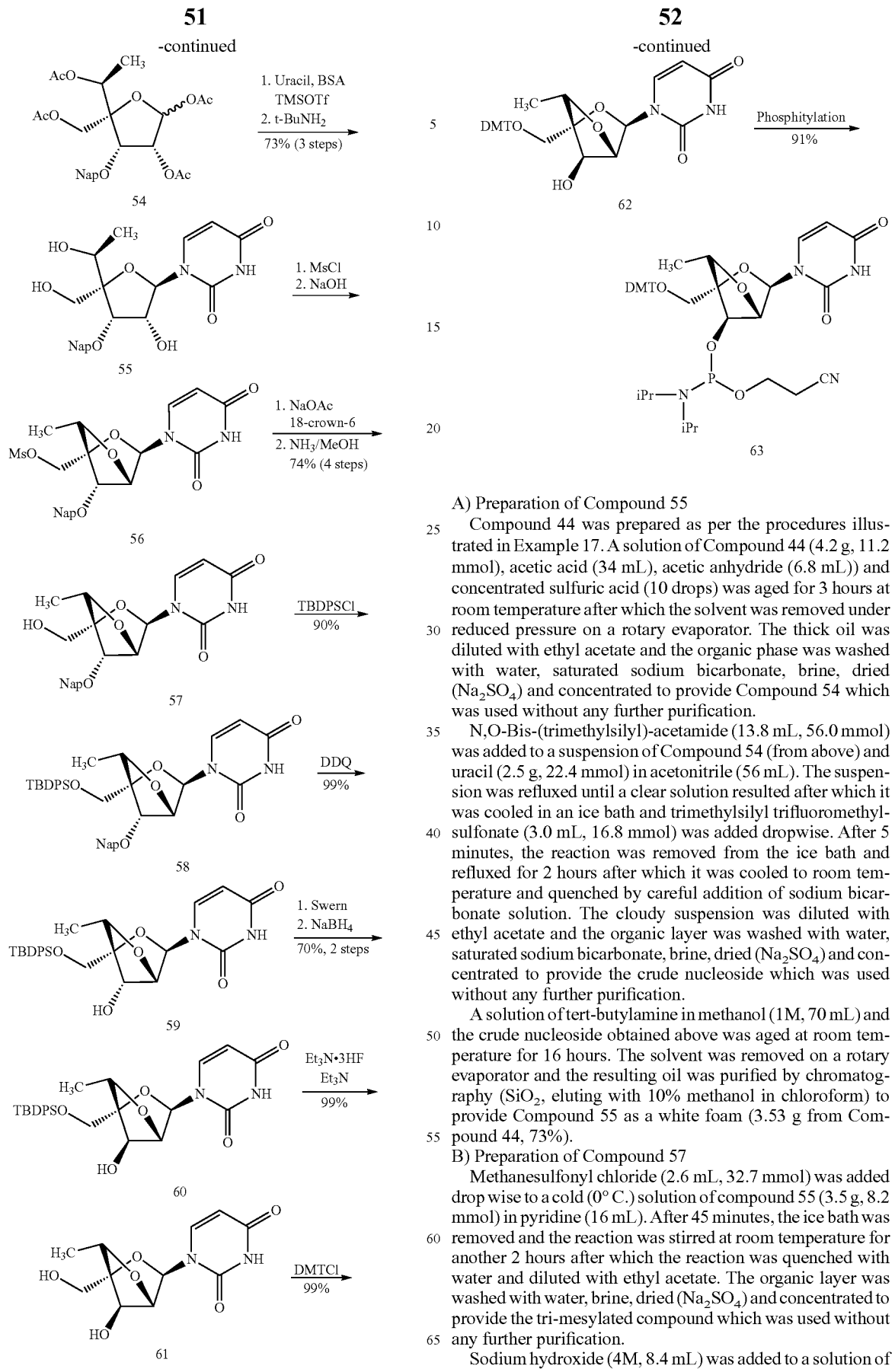

A) Preparation of Compound 55

Compound 44 was prepared as per the procedures illustrated in Example 17. A solution of Compound 44 (4.2 g, 11.2 mmol), acetic acid (34 mL), acetic anhydride (6.8 mL)) and concentrated sulfuric acid (10 drops) was aged for 3 hours at room temperature after which the solvent was removed under reduced pressure on a rotary evaporator. The thick oil was diluted with ethyl acetate and the organic phase was washed with water, saturated sodium bicarbonate, brine, dried (Na$_2$SO$_4$) and concentrated to provide Compound 54 which was used without any further purification.

N,O-Bis-(trimethylsilyl)-acetamide (13.8 mL, 56.0 mmol) was added to a suspension of Compound 54 (from above) and uracil (2.5 g, 22.4 mmol) in acetonitrile (56 mL). The suspension was refluxed until a clear solution resulted after which it was cooled in an ice bath and trimethylsilyl trifluoromethylsulfonate (3.0 mL, 16.8 mmol) was added dropwise. After 5 minutes, the reaction was removed from the ice bath and refluxed for 2 hours after which it was cooled to room temperature and quenched by careful addition of sodium bicarbonate solution. The cloudy suspension was diluted with ethyl acetate and the organic layer was washed with water, saturated sodium bicarbonate, brine, dried (Na$_2$SO$_4$) and concentrated to provide the crude nucleoside which was used without any further purification.

A solution of tert-butylamine in methanol (1M, 70 mL) and the crude nucleoside obtained above was aged at room temperature for 16 hours. The solvent was removed on a rotary evaporator and the resulting oil was purified by chromatography (SiO$_2$, eluting with 10% methanol in chloroform) to provide Compound 55 as a white foam (3.53 g from Compound 44, 73%).

B) Preparation of Compound 57

Methanesulfonyl chloride (2.6 mL, 32.7 mmol) was added drop wise to a cold (0° C.) solution of compound 55 (3.5 g, 8.2 mmol) in pyridine (16 mL). After 45 minutes, the ice bath was removed and the reaction was stirred at room temperature for another 2 hours after which the reaction was quenched with water and diluted with ethyl acetate. The organic layer was washed with water, brine, dried (Na$_2$SO$_4$) and concentrated to provide the tri-mesylated compound which was used without any further purification.

Sodium hydroxide (4M, 8.4 mL) was added to a solution of the tri-mesylated compound from above in 1,4-dioxane (40 mL). After stirring at room temperature for 24 hours, the reaction was neutralized using aqueous hydrochloric acid and diluted with ethyl acetate. The organic layer was washed with water, brine, dried (Na$_2$SO$_4$) and concentrated to provide the cyclized Compound 56 which was used without any further purification A suspension of crude nucleoside 56 from above, potassium acetate (3.9 g, 40.0 mmol) and 18-crown-6 (4.2 g, 16.0 mmol) in 1,4-dioxane (80 mL) was refluxed for 24 hours after which it was cooled to room temperature and diluted with ethyl acetate. The organic layer was washed with water, brine, dried (Na$_2$SO$_4$) and concentrated to provide the 5'-acetoxy nucleoside which was used without any further purification.

A solution of the crude nucleoside from above in methanolic ammonia (7N, 50 mL) was aged at room temperature in a sealed vessel for 16 hours. The solvent was then removed on a rotary evaporator and the crude product was purified by chromatography (SiO$_2$, eluting with 5 to 10% methanol in chloroform) to provide Compound 57 (2.43 g, 74% from Compound 55).

C) Preparation of Compound 58 tert-Butyldiphenylsilyl chloride (2.1 mL, 8.4 mmol) was added to a solution of Compound 57 (1.73 g, 4.2 mmol) and imidazole (1.1 g, 16.8 mmol) in DMF (8.5 mL). After stirring at room temperature for 16 hours, the reaction was diluted with ethyl acetate and the organic layer was washed with water, brine, dried (Na$_2$SO$_4$) and concentrated. Purification by column chromatography (SiO$_2$, eluting with 5 to 10% acetone in chloroform) provided Compound 58 (2.4 g, 91%).

D) Preparation of Compound 59

DDQ (1.7 g, 7.5 mmoL) was added to a biphasic solution of Compound 58 (2.4 g, 3.8 mmol) in dichloromethane (38 mL) and water (2 mL). After stirring at room temperature for 16 hours, the solvent was removed on a rotary evaporator and the residue was dissolved in ethyl acetate. The organic layer was washed with 10% sodium bisulfite solution, saturated sodium bicarbonate, dried (Na$_2$SO$_4$) and concentrated. Purification by column chromatography (SiO$_2$, eluting with 25 to 35% acetone in chloroform) provided Compound 59 (1.91 g, 99%).

E) Preparation of Compound 60

Oxalyl chloride (0.7 mL, 7.5 mmol) was added drop wise to a cold (−78° C.) solution of dimethylsulfoxide (1.1 mL, 15.0 mmol) in dichloromethane (30 mL). After stirring for 30 minutes, a solution of Compound 59 (1.9 g, 3.8 mmol) in dichloromethane (10 mL) was added and the stirring was continued for another 45 minutes. Triethylamine (3.2 mL, 22.5 mmol) was then added over 10 minutes to the reaction. After the addition was complete, the reaction flask was then removed from the cold bath and stirred for another 30 minutes. The reaction was diluted with dichloromethane and the organic layer was washed with 5% HCl, saturated sodium bicarbonate, brine, dried (Na$_2$SO$_4$) and concentrated to provide the ketone which was used without any further purification.

Sodium borohydride (1.0 g pellet, 42.0 mmol) was added to a solution of the crude ketone (from above) in methanol (40 mL). After stirring at room temperature for 16 hours, the reaction was quenched by careful addition of 5% hydrochloric acid and the solvent was evaporated on a rotary evaporator. The residue was dissolved in ethyl acetate and the organic layer was washed with water, saturated sodium bicarbonate, brine, dried (Na$_2$SO$_4$) and concentrated. Purification by chromatography (SiO$_2$, eluting with 20 to 30% acetone in chloroform) provided Compound 60 (1.33 g, 70% from Compound 59).

F) Preparation of Compound 61

Triethylamine trihydrofluoride (2.6 mL, 15.7 mmol) was added to a solution of Compound 60 (1.33 g, 2.6 mmol) and triethylamine (0.92 mL, 6.6 mmol) in THF (26 mL). After stirring at room temperature for 48 hours, the solvent was removed on a rotary evaporator and the thick oil was purified by chromatography (SiO$_2$, eluting with 5 to 15% methanol in chloroform) to provide Compound 61 (0.71 g, 99%).

G) Preparation of Compound 62

4,4'-Dimethoxytrityl chloride (1.1 g, 3.3 mmol) was added to a solution of Compound 61 (0.71 g, 2.6 mmol) in pyridine (13 mL). After stirring at room temperature for 16 hours, the reaction was diluted with ethyl acetate and the organic layer was washed with water, brine, dried (Na$_2$SO$_4$) and concentrated. Purification by chromatography (SiO$_2$, eluting with 20 to 33% acetone in chloroform) provided Compound 62 (1.47 g, 99%).

H) Preparation of Compound 63

2-cyanoethyl-N,N,N',N'-tetraisopropylphosphoramidite (0.55 mL, 1.8 mmol) was added to a solution of Compound 62 (0.67 g, 1.2 mmol), tetrazole (65.0 mg, 0.93 mmol), N-methylimidazole (24 µL, 0.3 mmol) in DMF (6 mL). After stirring for 8 hours at room temperature, the reaction was poured into EtOAc and the organic phase was washed with brine, dried (Na$_2$SO$_4$) and concentrated. Purification by column chromatography (SiO$_2$, eluting with 60% EtOAc/hexanes-75% EtOAc/hexanes) gave Compound 63 (0.91 g, 87%) as a white solid.

Compound 63 $^{31}$P NMR (300 MHz, CDCl$_3$) δ: 150.3, 149.9.

Example 20

Preparation of (1R,3R,4S,6R,7R)-7-[2-cyanoethoxy (diisopropylamino)phosphinoxy]-1-(4,4'-dimethoxytrityloxymethylenyl)-3-(4-N-benzoylcytosin-1-yl)-6-methyl-2,5-dioxa-bicyclo-[2.2.1]heptane (Compound 67)

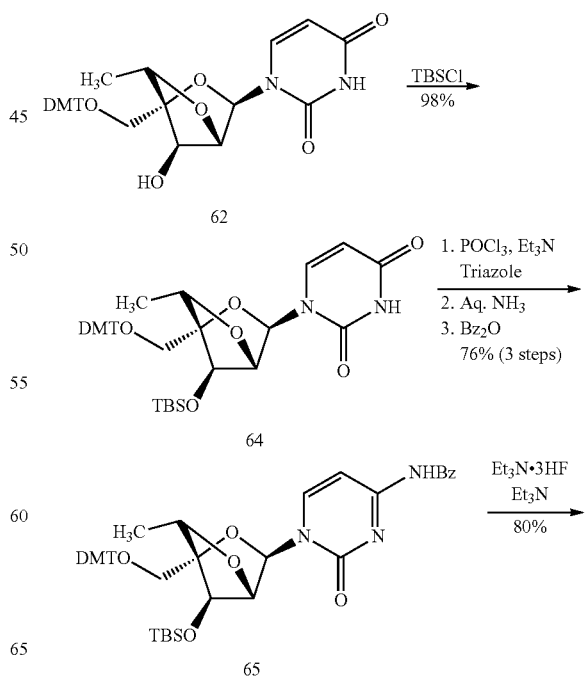

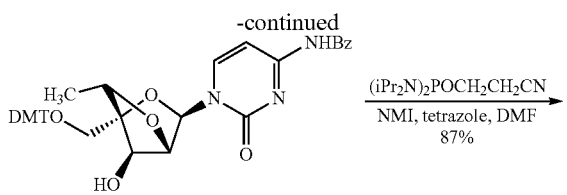

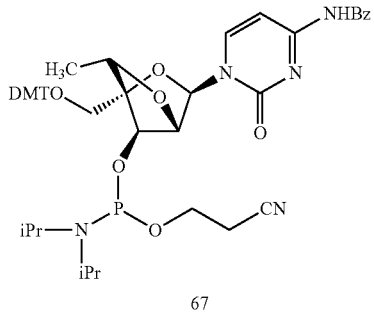

A) Preparation of Compound 64

Compound 62 was prepared as per the procedures illustrated in Example 19. tert-Butyldimethylsilyl chloride (0.42 g, 2.8 mmol) was added to a solution of Compound 62 (0.8 g, 1.4 mmol) and imidazole (0.38 g, 5.6 mmol) in DMF (3 mL). After stirring at room temperature for 16 hours, the reaction was diluted with ethyl acetate and the organic layer was washed with water, brine, dried (Na$_2$SO$_4$) and concentrated. Purification by column chromatography (SiO$_2$, eluting with 10 to 15% acetone in chloroform) provided Compound 64 (0.93 g, 98%).

B) Preparation of Compound 65

Phosphorus oxychloride (1.0 mL, 10.8 mmol) was added to a cold (0° C.) solution of 1,2,4-triazole (3.2 g, 45.9 mmol) in acetonitrile (22 mL). After stirring for 15 minutes, triethylamine (7.5 mL, 54.0 mmol) was added to the reaction and the suspension was stirred for another 30 minutes. A solution of Compound 64 (0.93 g, 1.4 mmol) in acetonitrile (10 mL) was added to the reaction and the ice bath was removed after the addition was complete. After stirring at room temperature for another 6 hours, the solvent was removed on a rotary evaporator and the reaction was diluted with ethyl acetate and the organic layer was washed with water, saturated sodium bicarbonate, brine, dried (Na$_2$SO$_4$) and concentrated to provide the crude triazolide which was used without any further purification.

The crude triazolide (from above) was dissolved in 1,4-dioxane (10 mL) and aqueous ammonia solution (2 mL). The reaction was aged for 16 hours in a sealed container and the solvent was removed on a rotary evaporator. The yellow foam was dried under high vacuum for 16 hours and used without any further purification.

Benzoic anhydride (0.46 g, 2.0 mmol) was added to a solution of crude nucleoside (from above) in DMF (3 mL). After stirring at room temperature for 16 hours, the reaction was diluted with ethyl acetate and the organic layer was washed with water, brine, dried (Na$_2$SO$_4$) and concentrated. Purification by column chromatography (SiO$_2$, eluting with 50% ethyl acetate in hexanes) provided Compound 65 (0.81 g, 76% from Compound 64).

C) Preparation of Compound 66

Triethylamine trihydrofluoride (1.0 mL, 6.1 mmol) was added to a solution of Compound 65 (0.81 g, 1.0 mmol) and triethylamine (0.4 mL, 2.6 mmol) in THF (10 mL). After stirring at room temperature for 48 hours, the reaction was diluted with ethyl acetate and the organic layer was washed with water, saturated sodium bicarbonate, brine, dried (Na$_2$SO$_4$) and concentrated. Purification by chromatography (SiO$_2$, eluting with 40 to 50% acetone in chloroform) provided Compound 66 (0.55 g, 80%).

D) Preparation of compound 67

2-cyanoethyl-N,N,N',N'-tetraisopropylphosphoramidite (0.4 mL, 1.2 mmol) was added to a solution of compound 66 (0.55 g, 0.8 mmol), tetrazole (46.0 mg, 0.66 mmol), N-methylimidazole (17 μL, 0.21 mmol) in DMF (4 mL). After stirring for 8 hours at room temperature, the reaction was poured into EtOAc and the organic phase was washed with brine, dried (Na$_2$SO$_4$) and concentrated. Purification by column chromatography (SiO$_2$, eluting with 75 to 90% ethyl acetate in hexanes) gave Compound 67 (0.63 g, 87%) as a white solid.

Compound 67 $^{31}$P NMR (300 MHz, CDCl$_3$) δ: 150.6, 150.0.

Example 21

Preparation of (1R,3R,4S,7R)-7-[2-cyanoethoxy-(diisopropylamino)phosphinoxy]-1-(4,4'-dimethoxytrityloxymethylenyl)-3-(uracil-1-yl)-3-methyl-2,5-dioxa-bicyclo[2.2.1]heptane (Compound 76)

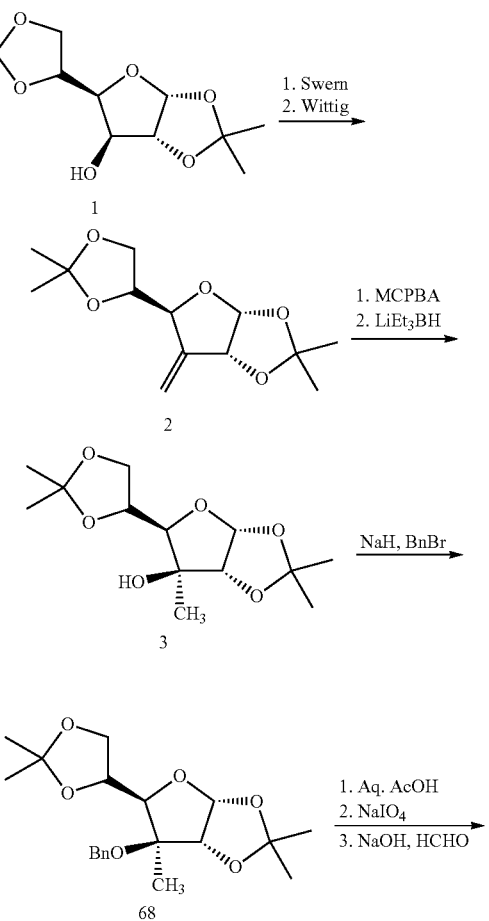

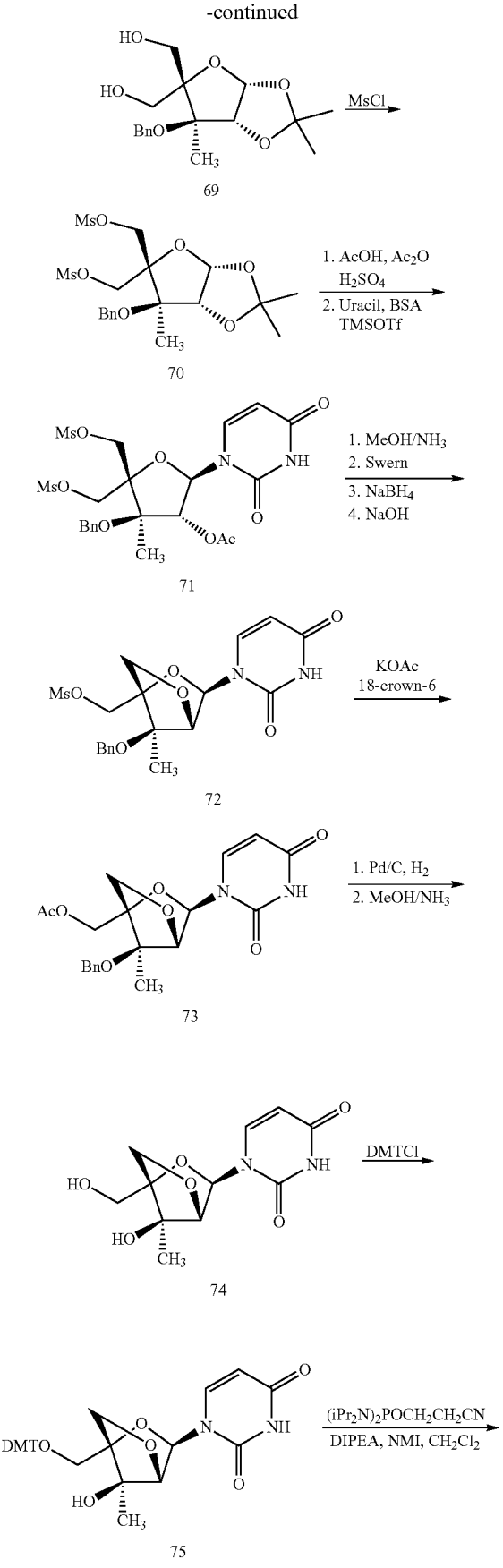

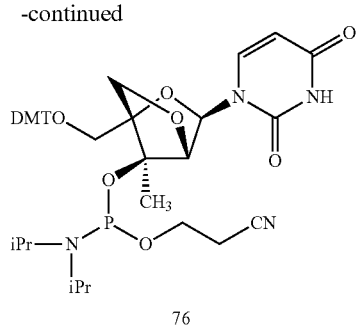

A) Preparation of Compound 2

Compound 1, 1,2:5,6-di-O-isopropylidene-α-D-glucose-furanose is commercially available (Ferro Pfanstiehl Laboratories, Inc). Oxalyl chloride (21.7 mL, 250.0 mmol) was added drop wise to a cold (−78° C.) solution of dimethylsulfoxide (35.5 mL, 500.0 mmol) in dichloromethane (900 mL). After stirring for 30 minutes, a solution of Compound 1 (50.0 g, 192.0 mmol) in dichloromethane (100 mL) was added and the stirring was continued for another 45 minutes. Triethylamine (105.0 mL, 750.0 mmol) was then added over 10 minutes to the reaction. After the addition was complete, the reaction flask was then removed from the cold bath and stirred for another 30 minutes. The reaction was diluted with dichloromethane and the organic layer was washed with 5% HCl, saturated sodium bicarbonate, brine, dried ($Na_2SO_4$) and concentrated to provide the ketone which was used without any further purification.

n-BuLi (250 mmol, 100 mL of a 2.5 M solution) was added to a cold (0° C.) suspension of methyltriphosphonium bromide (89.3 g, 250 mmol) in THF (900 mL). After stirring for 1 hour, the dark red solution was cooled (−78° C.) and a solution of the ketone from above in THF (100 mL) was added via a cannula. The reaction was gradually allowed to reach room temperature and the stirring was continued for another 16 hours. The reaction was carefully quenched with ammonium chloride solution and roughly half of the solvent was removed on a rotary evaporator. The reaction was diluted with ethyl acetate and the organic layer was washed with water, brine, dried ($Na_2SO_4$) and concentrated. Purification by chromatography ($SiO_2$, eluting with hexanes to 20% ethyl acetate in hexanes) provided Compound 2 (46.0 g, 92% from Compound 1).

B) Preparation of Compound 3 meta-Chloroperbenzoic acid (123.0 g, 718 mmol, ~77% by weight) was added to a solution of compound 2 (46.0 g, 180 mmol) in dichloromethane (1 L). After stirring for 4 days at room temperature, additional meta-chloroperbenzoic acid (25 g) was added to the reaction and the stirring was continued for another 2 days. The solvent was removed on a rotary evaporator and the thick oil was redissolved in ethyl acetate and the organic layer was washed with 10% sodium thiosulfate/10% sodium bicarbonate (1:1), brine, dried ($Na_2SO_4$) and concentrated. Purification by chromatography ($SiO_2$, eluting with hexanes to 20% ethyl acetate in hexanes) provided the major epoxide isomer (47.0 g of a roughly 10:1 mixture of major epoxide isomer and Compound 2 and ~10% by weight of unreacted meta-chloroperbenzoic acid). $^1$H NMR of major epoxide isomer (300 MHz, $CDCl_3$) δ: 5.94 (d, 1H, J=3.9 Hz), 4.37 (d, 1H, J=6.8 Hz), 4.29 (d, 1H, J=3.9 Hz), 4.07-3.99 (m, 3H), 3.16 (d, 1H, J=4.8 Hz), 3.09 (d, 1H, J=4.8), 1.56 (s, 3H), 1.4 (s, 3H), 1.33 (s, 3H), 1.31 (s, 3H).

Super hydride (200 mL of a 1M solution of LiBEt$_3$H) was added to a cold (0° C.) solution of the partially purified mixture of the major epoxide isomer (47 g) from above in THF (175 mL). After the addition was complete, the cooling bath was removed and the stirring was continued at room temperature for 6 hours after which the reaction was carefully quenched with ammonium chloride solution. Roughly, half the solvent was removed on a rotary evaporator and the reaction was diluted with ethyl acetate and the organic layer was washed with 5% HCl solution, saturated sodium bicarbonate, brine, dried (Na$_2$SO$_4$) and concentrated. Purification by column chromatography (SiO$_2$, eluting with 10 to 40% ethyl acetate in hexanes) provided Compound 3 (31.7 g, 69% from Compound 2).

C) Preparation of Compound 68

Sodium hydride (6.94 g, 173.5 mmol, 60% in mineral oil) was added in portions over 15 minutes to a cold (0° C.) solution of Compound 3 (31.7 g, 115.7 mmol) and benzyl bromide (16.5 mL, 139 mmol) in DMF (120 mL). After the addition was complete, the reaction was stirred for another 2 hours after which it was carefully quenched with water. The reaction was diluted with ethyl acetate and the organic layer was washed with water, brine, dried (Na$_2$SO$_4$) and concentrated. Purification by chromatography (SiO$_2$, eluting with hexanes to 20% ethyl acetate in hexanes) provided Compound 68 (41.4 g, 98%).

D) Preparation of Compound 69

A solution of compound 68 (41.4 g, 115 mmol) in acetic acid (200 mL) and water (120 mL) was stirred at room temperature for 14 hours after which the reaction was partitioned between ethyl acetate and water. The organic layer was further washed with water, 1M sodium hydroxide, brine, dried (Na$_2$SO$_4$) and concentrated to provide the 5,6-diol which was used without any further purification.

Sodium periodate (27.0 g, 126.5 mmol) was added to a solution of the diol from above in 1,4-dioxane (400 mL) and water (800 mL). After stirring for 1 hour at room temperature, the reaction was partitioned between ethyl acetate and water and the organic layer was washed with brine, dried (Na$_2$SO$_4$) and concentrated to provide the 5-aldehyde which was used without any further purification.

Sodium hydroxide (50 mL of a 4 M solution) was added drop wise to a cold (0° C.) solution of the aldehyde from above and formaldehyde (100 mL of 37% solution in water) in dioxane (200 mL). After the addition was complete, the ice bath was removed and the reaction was stirred at room temperature for 2 days after which it was partitioned between ethyl acetate and water. The organic layer was washed with water, brine, dried (Na$_2$SO$_4$) and concentrated. Purification by chromatography (SiO$_2$, eluting with 10 to 30% acetone in chloroform) provided Compound 69 (6.9 g of a partially pure solid).

E) Preparation of Compound 70

Methanesulfonyl chloride (4.2 mL, 53.0 mmol) was added drop wise to a cold (0° C.) solution of Compound 69 (6.9 g, 21.2 mmol), triethylamine (7.4 mL, 53.0 mmol) and 4-dimethylaminopyridine (0.64 g, 5.3 mmol) in dichloromethane (100 mL). After stirring for 2 hours, the reaction was diluted with dichloromethane and the organic layer was washed with 5% HCl, saturated sodium bicarbonate, brine, dried (Na$_2$SO$_4$) and concentrated. Purification by column chromatography (SiO$_2$, eluting with 30 to 50% ethyl acetate in hexanes) provided Compound 70 (4.52 g, 44%).

F) Preparation of Compound 71

A solution of Compound 70 (4.5 g, 9.4 mmol), acetic acid (28 mL), acetic anhydride (5.6 mL) and concentrated sulfuric acid (6 drops) was aged at room temperature for 4 hours and the solvent was removed using a rotary evaporator. The oil was dissolved in ethyl acetate and the organic layer was washed with water, saturated sodium bicarbonate, brine, dried (Na$_2$SO$_4$) and concentrated to provide an anomeric mixture of diacetates which was used without any further purification.

N,O-Bis-(trimethylsilyl)-acetamide (11.0 mL, 45.0 mmol) was added to a suspension of diacetates (from above) and uracil (2.0 g, 18.0 mmol) in acetonitrile (45 mL). The suspension was refluxed until a clear solution resulted after which it was cooled in an ice bath and trimethylsilyl trifluoromethylsulfonate (2.8 mL, 18.0 mmol) was added dropwise. After 5 minutes, the reaction was removed from the ice bath and refluxed for 2 hours after which it was cooled to room temperature and quenched by careful addition of sodium bicarbonate solution. The cloudy suspension was diluted with ethyl acetate and the organic layer was washed with water, saturated sodium bicarbonate, brine, dried (Na$_2$SO$_4$) and concentrated. Purification by column chromatography (SiO$_2$, eluting with 10 to 20% acetone in dichloromethane) provided Compound 71 (4.2 g, 81% from Compound 70).

G) Preparation of Compound 72

Methanolic ammonia (35 mL of a 7N solution) was added to a solution of Compound 71 (4.2 g, 7.3 mmol) in 1,4-dioxane (10 mL) and the mixture was aged for 90 minutes at room temperature. The solvent was then removed on a rotary evaporator and the resulting foam was dried under high vacuum for 16 hours and used without any further purification.

Oxalyl chloride (1.3 mL, 14.5 mmol) was added drop wise to a cold (−78° C.) solution of dimethylsulfoxide (2.1 mL, 29.0 mmol) in dichloromethane (73 mL). After stirring for 30 minutes, a solution of the nucleoside from above in dichloromethane (10 mL) was added and the stirring was continued for another 45 minutes. Triethylamine (6.1 mL, 43.5 mmol) was then added over 10 minutes to the reaction. After the addition was complete, the reaction flask was then removed from the cold bath and stirred for another 30 minutes. The reaction was diluted with dichloromethane and the organic layer was washed with 5% HCl, saturated sodium bicarbonate, brine, dried (Na$_2$SO$_4$) and concentrated to provide the ketone which was used without any further purification.

Sodium borohydride (100 mg) was added to a cold (−78° C.) solution of the ketone from above in methanol (50 mL). After stirring for 2 hours, the reaction was quenched with 5% HCl solution and the solvent was evaporated on a rotary evaporator. The thick oil was dissolved in ethyl acetate and the organic layer was washed with water, saturated sodium bicarbonate, brine, dried (Na$_2$SO$_4$) and concentrated to provide the crude nucleoside which was used without any further purification.

A solution of crude nucleoside from above in 1,4-dioxane (70 mL) and 4M sodium hydroxide (7 mL) was stirred at room temperature for 16 hours after which the reaction was neutralized with 5% HCl solution. The reaction was then partitioned between ethyl acetate and water and the organic layer was washed with brine, dried (Na$_2$SO$_4$) and concentrated. Purification by chromatography (SiO$_2$, eluting with 30 to 40% acetone in chloroform) provided Compound 72 (61% from Compound 71).

H) Preparation of Compound 73

A suspension of compound 72 (1.93 g, 4.4 mmol), potassium acetate (4.3 g, 44.0 mmol) and 18-crown-6 (5.8 g, 22.0 mmol) in 1,4-dioxane (20 mL) was refluxed for 2 days. The reaction was cooled to room temperature and diluted with ethyl acetate. The organic layer was washed with water, brine, dried (Na$_2$SO$_4$) and concentrated. Purification by chromatography (SiO$_2$, eluting with 10 to 30% acetone in dichloromethane provided Compound 73 (1.36 g, 77%).

I) Preparation of Compound 74

A suspension of Compound 73 (1.36 g, 3.4 mmol) was hydrogenated using catalytic palladium on charcoal (10% w/w, 0.15 g) and a hydrogen balloon in methanol (20 mL) for 48 hours. The reaction was then filtered through a bed of celite and the bed was washed with additional methanol. The combined filtrates were concentrated on a rotary evaporator and used without any purification.

Methanolic ammonia (17 mL, 7N) was added to a solution of the crude nucleoside from above in 1,4-dioxane (7 mL). The reaction was aged at room temperature for 16 hours in a sealed vessel after which it was concentrated on a rotary evaporator. The residue was azeotroped with acetonitrile and the resulting solid was dried under high vacuum for 16 hours to provide Compound 74 which was used without any further purification.

J) Preparation of Compound 75

4,4'-Dimethoxytrityl chloride (1.76 g, 5.3 mmol) was added to a solution of Compound 74 from above in pyridine (15 mL). After stirring at room temperature for 16 hours, the reaction was diluted with ethyl acetate and the organic layer was washed with water, brine, dried (Na$_2$SO$_4$) and concentrated. Purification by chromatography (SiO$_2$, eluting with 10 to 50% acetone in chloroform) provided Compound 75 (1.45 g, 73% from Compound 74).

K) Preparation of Compound 76

2-cyanoethyl-N,N,N',N'-diisopropylchlorophosphoramidite (0.4 mL, 1.7 mmol) was added to a solution of compound 75 (0.5 g, 0.85 mmol), DIPEA (0.3 mL, 1.7 mmol) and N-methylimidazole (5 drops). After stirring for 2 hours at room temperature, the reaction was poured into EtOAc and the organic phase was washed with brine, dried (Na$_2$SO$_4$) and concentrated. Purification by column chromatography (SiO$_2$, eluting with 60 to 75% ethyl acetate in hexanes) gave Compound 76 (0.56 g, 84%) as a white solid.

Compound 76 $^{31}$P NMR (300 MHz, CDCl$_3$) δ: 145.2, 144.7.

Example 22

Preparation of (1R,3R,4S,7R)-7-[2-cyanoethoxy(diisopropylamino)phosphinoxy]-1-(4,4'-dimethoxytrityloxymethylenyl)-3-(4-N-benzoylcytosin-1-yl)-3-methyl-2,5-dioxa-bicyclo-[2.2.1]heptane (Compound 80)

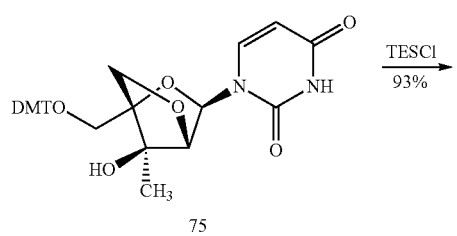

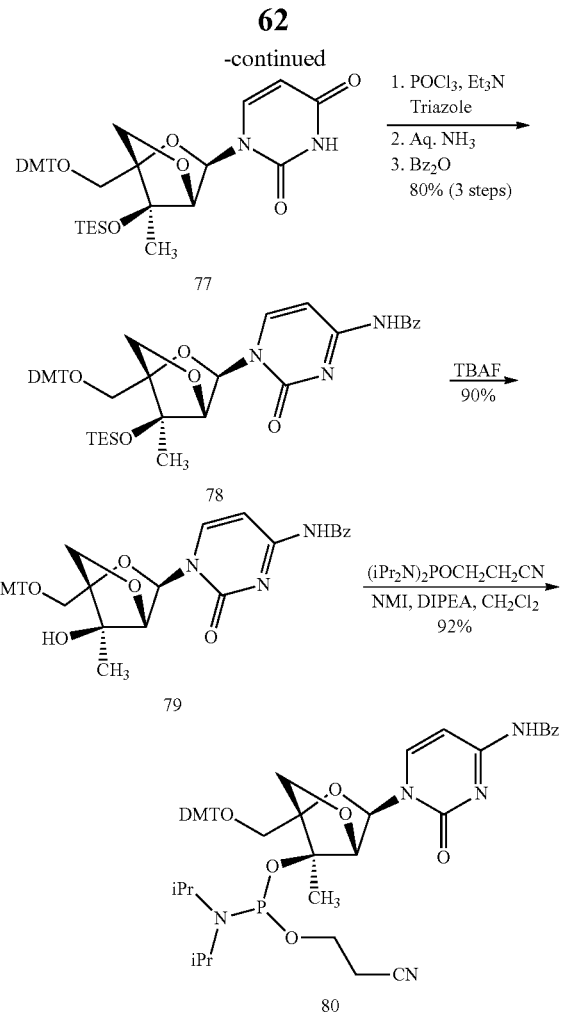

A) Preparation of Compound 77

Compound 75 was prepared as per the procedures illustrated in Example 21. tert-Triethylsilyl chloride (0.7 mL, 4.1 mmol) was added to a solution of Compound 75 (0.8 g, 1.4 mmol) and imidazole (0.56 g, 8.2 mmol) in DMF (7 mL). After stirring at room temperature for 48 hours, the reaction was diluted with ethyl acetate and the organic layer was washed with water, brine, dried (Na$_2$SO$_4$) and concentrated. Purification by column chromatography (SiO$_2$, eluting with 10 to 15% acetone in chloroform) provided Compound 77 (0.86 g, 93%).

B) Preparation of Compound 78

Phosphorus oxychloride (1.0 mL, 10.2 mmol) was added to a cold (0° C.) solution of 1,2,4-triazole (3.0 g, 42.8 mmol) in acetonitrile (25 mL). After stirring for 15 minutes, triethylamine (7.2 mL, 51.0 mmol) was added to the reaction and the suspension was stirred for another 30 minutes. A solution of Compound 77 (0.87 g, 1.3 mmol) in acetonitrile (10 mL) was added to the reaction and the ice bath was removed after the addition was complete. After stirring at room temperature for another 6 hours, the solvent was removed on a rotary evaporator and the reaction was diluted with ethyl acetate and the organic layer was washed with water, saturated sodium bicarbonate, brine, dried (Na$_2$SO$_4$) and concentrated to provide the crude triazolide which was used without any further purification.

The crude triazolide (from above) was dissolved in 1,4-dioxane (8 mL) and aqueous ammonia solution (4 mL). The reaction was aged for 16 hours in a sealed container and the solvent was removed on a rotary evaporator. The yellow foam was dried under high vacuum for 16 hours and used without any further purification.

Benzoic anhydride (0.13 g) was added to a solution of crude nucleoside (from above) in DMF (6 mL). After stirring at room temperature for 16 hours, the reaction was diluted with ethyl acetate and the organic layer was washed with water, brine, dried ($Na_2SO_4$) and concentrated. Purification by column chromatography ($SiO_2$, eluting with 50% ethyl acetate in hexanes) provided Compound 78 (0.80 g, 79% from Compound 77).

C) Preparation of Compound 79

Tetrabutylammonium fluoride (1.2 mL of a 1M solution) was added to a solution of compound 78 (0.8 g, 1.0 mmol) in THF (2 mL). After stirring at room temperature for 16 hours, the reaction was diluted with ethyl acetate and the organic layer was washed with water, saturated sodium bicarbonate, brine, dried ($Na_2SO_4$) and concentrated. Purification by chromatography ($SiO_2$, eluting with 10 to 20% acetone in chloroform) provided Compound 79 (0.61 g, 90%).

D) Preparation of compound 80

2-cyanoethyl-N,N,N',N'-diisopropylchlorophosphoramidite (0.4 mL, 1.8 mmol) was added to a solution of Compound 79 (0.6 g, 0.9 mmol), DIPEA (0.3 mL, 1.8 mmol) and N-methylimidazole (5 drops). After stirring for 2 hours at room temperature, the reaction was poured into EtOAc and the organic phase was washed with brine, dried ($Na_2SO_4$) and concentrated. Purification by column chromatography ($SiO_2$, eluting with 75 to 90% ethyl acetate in hexanes) gave Compound 80 (0.70 g, 92%) as a white solid.

Compound 80 $^{31}P$ NMR (300 MHz, $CDCl_3$) δ: 145.4, 144.8.

Example 23

Preparation of 3-O-Naphthylmethyl-5-O-tertbutyl-diphenylsilyl-4-(hydroxymethyl)-1,2-O-isopropylidene -α-D-threo-pentofuranose (Compound 86)

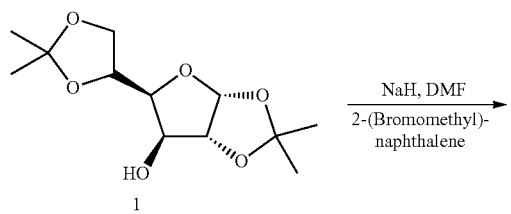

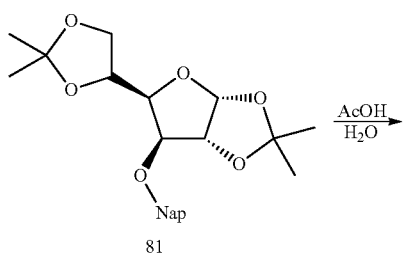

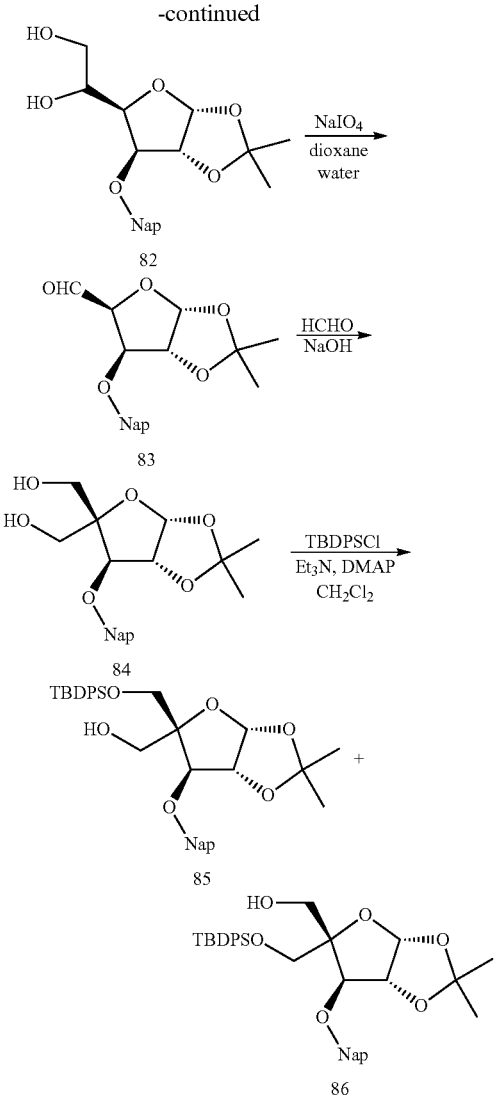

A) Preparation of Compound 81

Compound 1, 1,2:5,6-di-O-isopropylidene-α-D-glucosefuranose is commercially available (Ferro Pfanstiehl Laboratories, Inc). Sodium hydride (11.5 g, 288.0 mmol, 60% w/w) was carefully added in portions over 30 minutes to a cold (0° C.) solution of Compound 1 (50.0 g, 192.0 mmol) in DMF (200 mL). After stirring for 30 minutes, a solution of 2-(bromomethyl)-naphthalene (43.7 g, 197.8 mmol) in DMF (50 mL) was added to the reaction and the stirring was continued for 16 hours at room temperature. The reaction was carefully quenched with ammonium chloride solution and diluted with ethyl acetate. The organic layer was washed with water, brine, dried ($Na_2SO_4$) and concentrated. Purification by chromatography ($SiO_2$, eluting with 20% ethyl acetate in hexanes) provided Compound 81 (80.0 g, quantitative yield).

B) Preparation of Compound 84

A solution of Compound 81 (63.0 g, 158.0 mmol) in acetic acid (900 mL) and water (360 mL) was stirred at room temperature for 14 hours the reaction was partitioned between ethyl acetate and water and the organic layer was further washed with water, 1M sodium hydroxide, brine, dried ($Na_2SO_4$) and concentrated to provide Compound 82 which was used without any further purification.

Sodium periodate (36.6 g, 170.0 mmol) was added to a solution of Compound 82 from above in 1,4-dioxane (600 mL) and water (1.2 L). After stirring for 1 hour at room temperature, the reaction was partitioned between ethyl acetate and water and the organic layer was washed with brine, dried ($Na_2SO_4$) and concentrated to provide Compound 83 which was used without any further purification.

Sodium hydroxide (250 mL of a 2 M solution) was added to a solution of Compound 83 from above and formaldehyde (100 mL of 37% solution in water) in a mixture of THF (200 mL) and water (200 mL). The reaction was stirred at room temperature for 2 days after which it was partitioned between ethyl acetate and water. The organic layer was washed with water, brine, dried ($Na_2SO_4$) and concentrated. The white solid that was formed was suspended in a mixture of hexanes and water and stirred vigorously for 2 hours. The solid was then collected by filtration and further washed with water and hexanes and dried under high vacuum to provide Compound 84 (46 g, 67% from Compound 81).

E) Preparation of Compounds 85 and 86 tert-Butyldiphenylchlorosilane (300.0 mmol, 76.5 mL) was added to a cold (0° C.) stirring solution of Compound 84 (250.0 mmol, 90.0 g) and triethylamine (300 mmol, 42.0 mL) in dichloromethane (1 L). After the addition was complete, the reaction was warmed to room temperature stirring was continued for 16 hours after which methanol (50 mL) was added (to quench the excess TBDPSCl) to the reaction and stirring was continued for another 2 hours at room temperature. The reaction was diluted with chloroform and the organic layer was washed with 10% HCl, saturated $NaHCO_3$, brine, dried ($Na_2SO_4$) and concentrated. Purification by chromatography ($SiO_2$, eluting with 20 to 75% dichloromethane in hexanes, followed by 2.5 to 25% acetone in dichloromethane) provided Compound 85 (44 g, 30%), Compound 86 (35 g, 23%) and a mixture of Compounds 85 and 86 (68 g, 46%).

Compound 85 $^1H$ NMR (300 MHz, $CDCl_3$) δ: 7.86-7.75 (m, 5H), 7.69-7.62 (m, 4H), 7.50-7.27 (m, 7H), 7.18-7.13 (m, 2H), 6.11 (d, 1H, J=4.6 Hz), 4.99 (m, 1H), 4.93 (d, 1H, J=11.5 Hz), 4.74 (d, 1H, J=11.5 Hz), 4.22 (d, 1H, J=2.7 Hz), 3.80 (d, 1H, J=10.4 Hz), 3.69-3.64 (m, 3H), 2.15 (t, 1H, J=6.8 Hz), 1.59 (s, 3H), 1.39 (s, 3H), 1.04 (s, 9H).

Example 24

Preparation of (1S,3R,4S,7R)-7-[2-cyanoethoxy(diisopropylamino)phosphinoxy]-1-[1-(S)-(4,4'-dimethoxytrityl)oxy-ethyl]-3-(uracil-1-yl)-2,5-dioxabicyclo[2.2.1]heptanes (Compound 96)

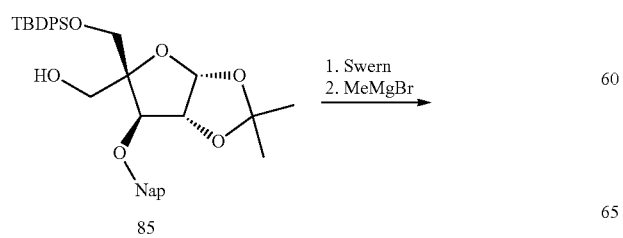

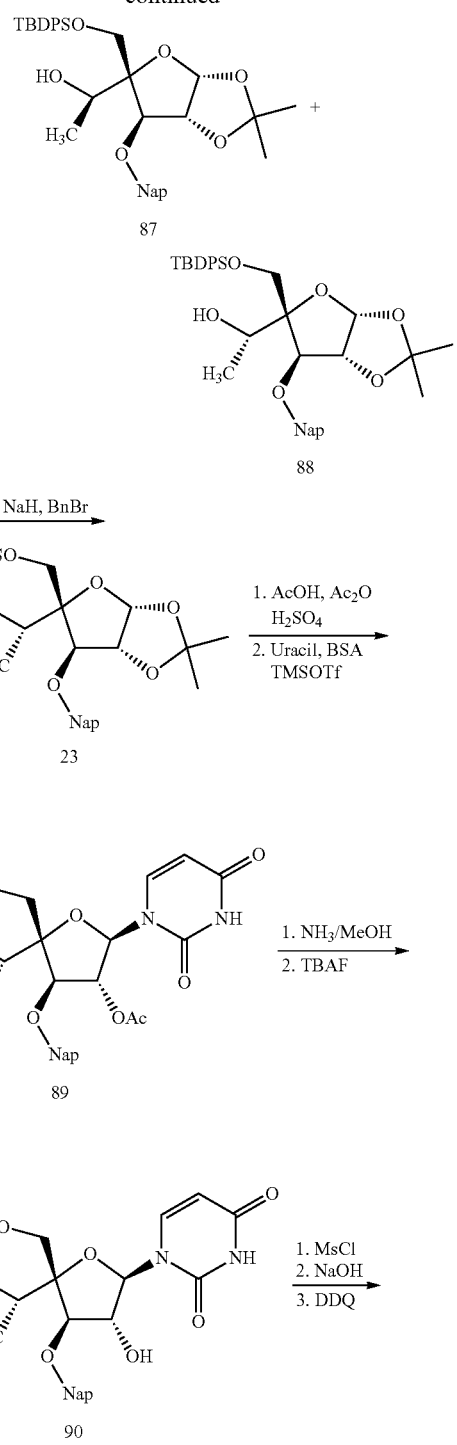

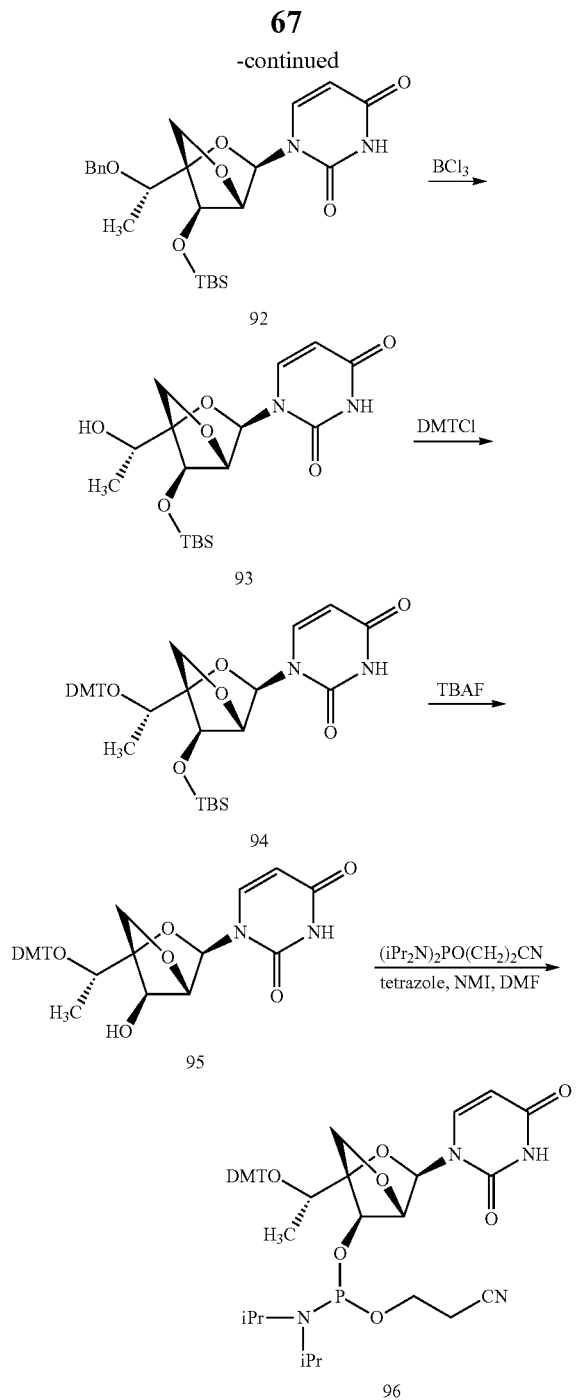

A) Preparation of Compounds 87 and 88

Compound 85 was prepared as per the procedures illustrated in Example 23. Dimethylsulfoxide (13.5 mL, 191.0 mmol) was added to a cold (−78° C.) solution of oxalyl chloride (8.3 mL, 95.6 mmol) in CH$_2$Cl$_2$ (500 mL). The solution was stirred at −78° C. for 30 minutes and a solution of Compound 85 (44.0 g, 73.6 mmol) in CH$_2$Cl$_2$ (250 mL) was added via a cannula. The stirring was continued for 45 minutes and triethylamine (40.0 mL, 286.0 mmol) was added to the reaction. The cooling bath was removed and the reaction was stirred for an additional 40 minutes after which it was poured into CH$_2$Cl$_2$ and the organic layer was sequentially washed with 5% aqueous HCl, saturated NaHCO$_3$, brine, dried (Na$_2$SO$_4$) and concentrated under vacuum to provide the corresponding aldehyde, which was used without purification in the next step.

Methyl magnesium bromide (75 mL of a 1.4 M solution in THF) was added to a cold (0° C.) solution of the aldehyde from above in THF (750 mL). After stirring for 1 hour, additional methyl magnesium bromide (15 mL) was added to the reaction. After stirring for an additional 30 minutes, the reaction was carefully quenched with ammonium chloride solution and partitioned between ethyl acetate and water. The organic phase was washed with 5% HCl, saturated sodium bicarbonate, brine, dried (Na$_2$SO$_4$) and concentrated. Purification by column chromatography (SiO$_2$, eluting with 5 to 25% ethyl acetate in hexanes) provided Compound 88 (16.0 g, 36% from Compound 85), Compound 87 (4.5 g, 10% from Compound 85) and a mixture of Compounds 87 and 88 (23.3 g, 51%).

Compound 88 $^1$H NMR (300 MHz, CDCl$_3$) δ: 7.89-7.77 (m, 4H), 7.71-7.67 (m, 2H), 7.64-7.59 (m, 2H), 7.52-7.43 (m, 3H), 7.43-7.33 (m, 3H), 7.30-7.18 (m, 2H), 7.12-7.03 (m, 2H), 6.14 (d, 1H, J=4.9 Hz), 5.11 (d, 1H, J=4.1 Hz), 4.99 (d, 1H, J=11.3 Hz), 4.75 (d, 1H, J=11.3 Hz), 4.38 (d, 1H, J=3.9 Hz), 3.89 (d, 1H, J=10.5 Hz), 3.82-3.7 (m, 1H), 3.44 (d, 1H, J=10.5 Hz), 2.70 (s, 1H), 1.63 (s, 3H), 1.42 (s, 3H), 1.05 (d, 3H, J=6.5), 1.01 (s, 9H).

B) Preparation of Compound 23

Sodium hydride (2.1 g, 52.0 mmol, 60% w/w in mineral oil) was added in portions to a cold (0° C.) solution of Compound 88 (16.0 g, 26.0 mmol) and benzyl bromide (15.4 g, 130.0 mmol) in DMF (130 mL). After stirring for 30 minutes, the reaction was carefully quenched with water and diluted with ethyl acetate. The organic layer was washed with water, brine, dried (Na$_2$SO$_4$) and concentrated. Purification by chromatography (SiO$_2$, eluting with hexanes to 10% ethyl acetate in hexanes) provided Compound 23 (18.2 g, 99%).

C) Preparation of Compound 89

A solution of Compound 23 (18.2 g, 26.0 mmol) in acetic acid (78 mL), acetic anhydride (15 mL) and concentrated sulfuric acid (10 drops) was aged for 5 hours at room temperature after which the solvent was removed on a rotary evaporator under high vacuum. The oil was redissolved in ethyl acetate and the organic layer was washed with water, brine, dried (Na$_2$SO$_4$) and concentrated to provide a mixture of anomeric diacetates which was used without any further purification.

N,O-Bis-(trimethylsilyl)-acetamide (22.9 mL, 93.6 mmol) was added to a suspension of the diacetate (from above) and uracil (4.4 g, 39.0 mmol) in acetonitrile (125 mL). The suspension was refluxed until a clear solution resulted after which it was cooled in an ice bath and trimethylsilyl trifluoromethylsulfonate (6.0 mL, 39.0 mmol) was added dropwise. After 5 minutes, the reaction was removed from the ice bath and refluxed for 2 hours after which it was cooled to room temperature and quenched by careful addition of sodium bicarbonate solution. The cloudy suspension was diluted with ethyl acetate and the organic layer was washed with water, saturated sodium bicarbonate, brine, dried (Na$_2$SO$_4$) and concentrated. Purification by column chromatography (SiO$_2$, eluting with 10 to 35% ethyl acetate in hexanes) provided Compound 89 (13.0 g, 65% from Compound 23).

D) Preparation of Compound 90

A solution of Compound 89 (13.0 g, 16.3 mmol) in methanolic ammonia (25 mL of a 7N solution) was aged in a sealed vessel for 16 hours at room temperature after which the solvent was evaporated on a rotary evaporator. The crude oil was redissolved in TBAF (55 mL of a 1M solution) and the reaction was stirred at room temperature for 16 hours after which it was diluted with ethyl acetate. The organic layer was then washed with water, brine, dried (Na$_2$SO$_4$) and concentrated. Purification by column chromatography (SiO$_2$, eluting with 10 to 30% acetone in dichloromethane) provided Compound 90 (7.2 g, 85% over 2 steps).

E) Preparation of Compound 91

Methanesulfonyl chloride (2.7 mL, 34.6 mmol) was added drop wise to a cold (0° C.) solution of Compound 90 (7.2 g, 13.9 mmol) in pyridine (69 mL). After stirring for 16 hours, the reaction was diluted with ethyl acetate and the organic layer was washed with water, brine, dried (Na$_2$SO$_4$) and concentrated to provide the bis-mesylate which was used without any further purification.

Sodium hydroxide (31 mL of a 4M solution) was added to a solution of the bis-mesylate from above in 1,4-dioxane (130 mL). After stirring at room temperature for 48 hours, the reaction was neutralized with 5% HCl and diluted with ethyl acetate. The organic layer was washed with water, brine, dried (Na$_2$SO$_4$) and concentrated to provide the cyclized nucleoside which was used without any further purification.

DDQ (4.1 g, 18.0 mmol) was added to a solution of cyclized nucleoside from above in dichloromethane (130 mL) and water (7 mL). After stirring at room temperature for 16 hours, the solvent was removed on a rotary evaporator and the residue was suspended in a mixture of dichloromethane and 10% sodium bisulfate solution. The solid was collected by filtration and resuspended in a mixture of ethyl acetate and saturated sodium bicarbonate solution. The solid was collected by filtration and then washed with a mixture of ether and ethyl acetate. The solid was further dried under high vacuum to provide Compound 91 (6.1 g) which was used without any further purification.

F) Preparation of Compound 92 tert-Butyldimethylsilyl chloride (9.8 g, 65.0 mmol) was added to a solution of Compound 91 (6.1 g, 13.0 mmol) and imidazole (8.8 g, 130 mmol) in DMF (85 mL). After stirring at room temperature for 16 hours, the reaction was quenched with methanol and diluted with ethyl acetate. The organic layer was washed with water, brine, dried (Na$_2$SO$_4$) and concentrated. Purification by chromatography (SiO$_2$, eluting with 1 to 10% acetone in dichloromethane) provided Compound 92 (4.6 g, 75% from Compound 90).

G) Preparation of Compound 93

Boron trichloride (45 mL of a 1M solution in dichloromethane) was added dropwise to a cold (−78° C.) solution of Compound 92 (4.3 g, 9.1 mmol) in dichloromethane (180 mL). After stirring for 90 minutes during which the reaction warmed up to −55° C., the reaction was recooled to −78° C. and carefully quenched with a solution of triethylamine (23 mL) and methanol (23 mL) in dichloromethane (50 mL). The reaction was stirred for another 10 minutes after which it was diluted with dichloromethane and the organic layer was washed with saturated sodium bicarbonate, brine, dried (Na$_2$SO$_4$) and concentrated. Purification by chromatography (SiO$_2$, eluting with 15 to 40% acetone in dichloromethane) provided Compound 93 (2.9 g, 83%).

H) Preparation of Compound 94

A solution 4,4'-Dimethoxytrityl chloride (0.22 g, 0.7 mmol), Compound 93 (0.1 g, 0.26 mmol) and 2,6-lutidine (0.08 mL, 0.7 mmol) in pyridine (1.3 mL) was heated at 45° C. for 48 hours. The reaction was cooled to room temperature, quenched with methanol and diluted with ethyl acetate. The organic layer was washed with water, dried (Na$_2$SO$_4$) and concentrated. Purification by chromatography (SiO$_2$, eluting with 35 to 50% ethyl acetate in hexanes) to provide Compound 94 (118 mg, 64%) and unreacted Compound 93 (16 mg, 16%).

I) Preparation of Compound 95

A solution of Compound 94 (118 mg, 0.17 mmol), triethylamine (0.06 mL, 0.4 mmol) and triethylamine trihydrofluoride (0.16 mL, 1.0 mmol) was stirred at room temperature for 24 hours after which it was diluted with ethyl acetate. The organic layer was washed with water, brine, dried (Na$_2$SO$_4$) and concentrated. Purification by column chromatography (SiO$_2$, eluting with 10 to 30% acetone in dichloromethane) provided Compound 95 (84 mg, 87%).

J) Preparation of Compound 96

2-cyanoethyl-N,N,N',N'-tetraisopropylphosphoramidite (0.07 mL, 0.22 mmol) was added to a solution of Compound 95 (85 mg, 0.14 mmol), tetrazole (8 mg, 0.12 mmol), N-methylimidazole (1 drop) in DMF (0.7 mL). After stirring for 8 hours at room temperature, the reaction was poured into EtOAc and the organic phase was washed with brine, dried (Na$_2$SO$_4$) and concentrated. Purification by column chromatography (SiO$_2$, eluting with 50 to 60% ethyl acetate in hexanes) gave Compound 96 (77 mg, 68%) as a white solid.

Compound 96 $^{31}$P NMR (300 MHz, CDCl$_3$) δ: 148.3, 148.9.

Example 25

Preparation of (1S,3R,4S,7R)-7-[2-cyanoethoxy(diisopropylamino)phosphinoxy]-1-[1-(R)-(4,4'-dimethoxytrityl)oxy-ethyl]-3-(uracil-1-yl)-2,5-dioxabicyclo[2.2.1]heptanes (Compound 100)

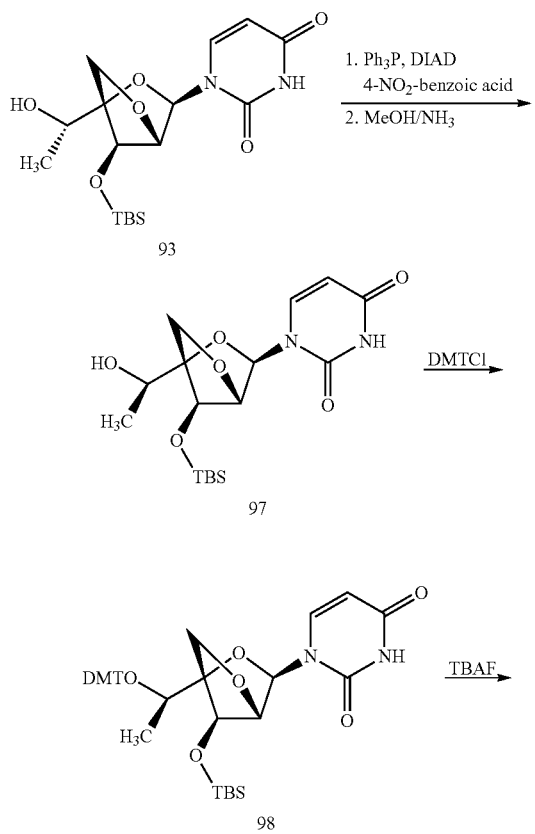

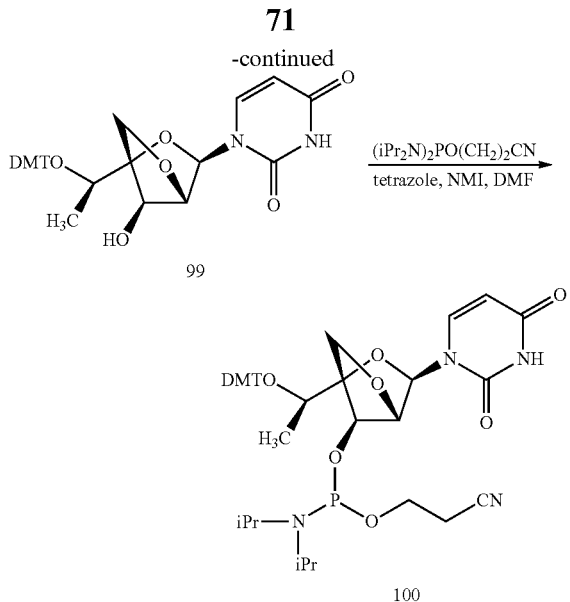

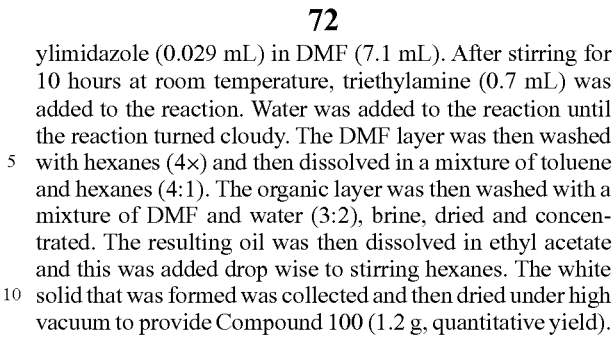

A) Preparation of Compound 97

Compound 93 was prepared as per the procedures illustrated in Example 24. Diisopropyl azodicarboxylate (DIAD, 2.5 g, 12.5 mmol) was added to a cold (0° C.) solution of Compound 93 (2.4 g, 6.3 mmol), triphenylphosphine (3.3 g, 12.5 mmol) and 4-nitrobenzoic acid (2.1 g, 12.5 mmol) in THF (100 mL). After stirring at room temperature for 2 hours, additional (DIAD, 0.63 mL), triphenylphosphine (0.82 g) and 4-nitrobenzoic acid (0.52 g) were added to the reaction and the stirring was continued for 16 hours at room temperature. The reaction was quenched with methanol and the solvent was removed on a rotary evaporator. Purification by column chromatography (SiO$_2$, eluting with 10 to 20% acetone in dichloromethane) provided the partially pure nitrobenzoate ester which was used without any further purification.

A solution of the ester from above and methanolic ammonia (50 mL of a 7N solution) was aged in a sealed vessel for 16 hours at room temperature after which the solvent was removed on a rotary evaporator to provide Compound 97 as a yellow foam which was used without any further purification.

B) Preparation of Compound 98

A solution of 4,4'-dimethoxytrityl chloride (5.0 g, 15.0 mmol), Compound 97 (from above) and 2,6-lutidine (1.7 mL, 15.0 mmol) in pyridine (30 mL) was heated at 45° C. for 3 days. The reaction was quenched with methanol and diluted with ethyl acetate and the organic layer was washed with water, brine, dried (Na$_2$SO$_4$) and concentrated. Purification by chromatography (SiO$_2$, eluting with 30 to 40% ethyl acetate in hexanes) provided Compound 98 (3.6 g, 84% from Compound 93) and unreacted Compound 97 (9% from Compound 93).

C) Preparation of Compound 99

Tetrabutylammonium fluoride (1.6 mL of a 1M solution) was added to a solution of Compound 98 (1.0 g, 3.2 mmol) in THF (1.5 mL). After stirring at room temperature for 1 hour, the reaction was diluted with ethyl acetate and the organic layer was washed with water, brine, dried (Na$_2$SO$_4$) and concentrated. Purification by chromatography (SiO$_2$, eluting with 10 to 30% acetone in dichloromethane) provided Compound 99 (0.68 g, 82%).

D) Preparation of Compound 100

2-cyanoethyl-N,N,N',N'-tetraisopropylphosphoramidite (0.64 mL, 2.2 mmol) was added to a solution of Compound 99 (0.64 g, 1.4 mmol), tetrazole (79 mg, 1.1 mmol), N-methylimidazole (0.029 mL) in DMF (7.1 mL). After stirring for 10 hours at room temperature, triethylamine (0.7 mL) was added to the reaction. Water was added to the reaction until the reaction turned cloudy. The DMF layer was then washed with hexanes (4x) and then dissolved in a mixture of toluene and hexanes (4:1). The organic layer was then washed with a mixture of DMF and water (3:2), brine, dried and concentrated. The resulting oil was then dissolved in ethyl acetate and this was added drop wise to stirring hexanes. The white solid that was formed was collected and then dried under high vacuum to provide Compound 100 (1.2 g, quantitative yield).

Compound 100 $^{31}$P NMR (300 MHz, CDCl$_3$) δ: 149.6, 149.0.

Example 26

Preparation of (1S,3R,4S,7R)-7-[2-cyanoethoxy(diisopropylamino)phosphinoxy]-1-[1-(R)-(4,4'-dimethoxytrityl)oxy-ethyl]-3-(-N-benzoylcytosin-1-yl)-2,5-dioxa-bicyclo[2.2.1]heptanes (Compound 103)

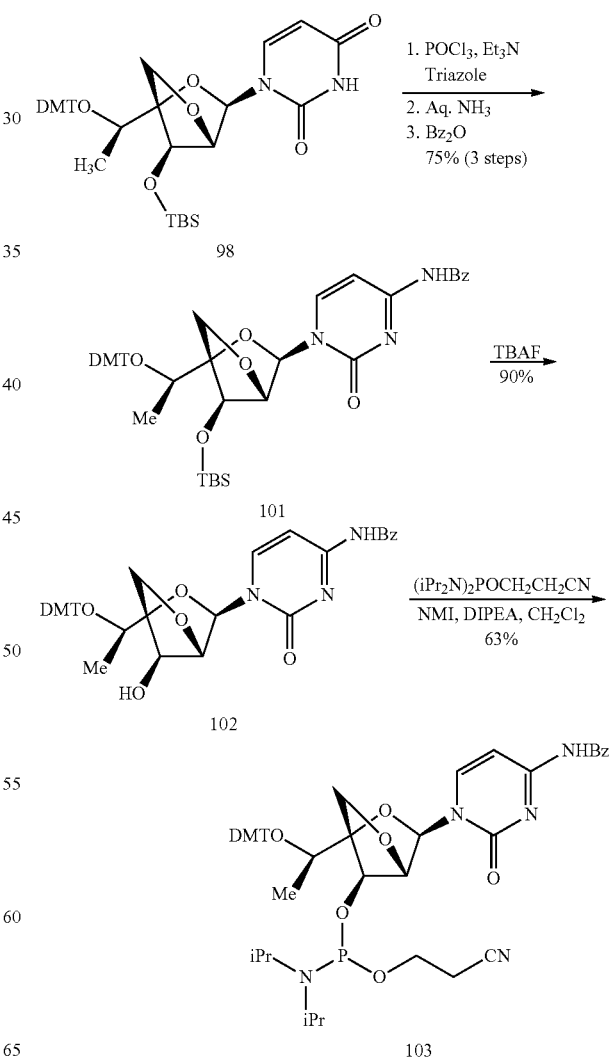

A) Preparation of Compound 101

Compound 98 was prepared as per the procedures illustrated in Example 25. Phosphorus oxychloride (1.6 mL, 17.5 mmol) was added to a cold (0° C.) solution of 1,2,4-triazole (5.1 g, 74.1 mmol) in acetonitrile (40 mL). After stirring for 15 minutes, triethylamine (12.2 mL, 87.2 mmol) was added to the reaction and the suspension was stirred for another 30 minutes. A solution of Compound 98 (1.5 g, 2.2 mmol) in acetonitrile (10 mL) was added to the reaction and the ice bath was removed after the addition was complete. After stirring at room temperature for another 6 hours, the solvent was removed on a rotary evaporator and the reaction was diluted with ethyl acetate and the organic layer was washed with water, saturated sodium bicarbonate, brine, dried ($Na_2SO_4$) and concentrated to provide the crude triazolide which was used without any further purification.

The crude triazolide (from above) was dissolved in 1,4-dioxane (22 mL) and aqueous ammonia solution (4 mL). The reaction was aged for 16 hours in a sealed container and the solvent was removed on a rotary evaporator. The yellow foam was dried under high vacuum for 16 hours and used without any further purification.

Benzoic anhydride (0.13 g) was added to a solution of crude nucleoside (from above) in DMF (6 mL). After stirring at room temperature for 16 hours, the reaction was diluted with ethyl acetate and the organic layer was washed with water, brine, dried ($Na_2SO_4$) and concentrated. Purification by column chromatography ($SiO_2$, eluting with 30 to 50% ethyl acetate in hexanes) provided Compound 101 (1.3 g, 76% from Compound 98).

B) Preparation of Compound 102

Tetrabutylammonium fluoride (1.9 mL of a 1M solution) was added to a solution of Compound 101 (1.3 g, 1.6 mmol) in THF (4 mL). After stirring at room temperature for 16 hours, the reaction was diluted with ethyl acetate and the organic layer was washed with water, saturated sodium bicarbonate, brine, dried ($Na_2SO_4$) and concentrated. Purification by chromatography ($SiO_2$, eluting with 10 to 20% acetone in chloroform) provided Compound 102 (0.98 g, 90%).

C) Preparation of Compound 103

2-cyanoethyl-N,N,N',N'-tetraisopropylphosphoramidite (0.7 mL, 2.2 mmol) was added to a solution of Compound 102 (0.97 g, 1.4 mmol), tetrazole (80 mg, 1.1 mmol), N-methylimidazole (0.03 mL, 0.4 mmol) in DMF (7.5 mL). After stirring for 8 hours at room temperature, the reaction was poured into EtOAc and the organic phase was washed with brine, dried ($Na_2SO_4$) and concentrated. Purification by column chromatography ($SiO_2$, eluting with 75 to 80% ethyl acetate in hexanes) gave Compound 103 (0.79 g, 63%) as a white solid.

Compound 103 $^{31}P$ NMR (300 MHz, $CDCl_3$) δ:149.6, 149.0.

Example 27

2-10-2 Gapped Oligomeric Compounds Targeted to PTEN: in vivo Study

Six week old Balb/c mice (Jackson Laboratory, Bar Harbor, Me.) were injected twice weekly for three weeks with gapped oligomeric compounds 400844 and 392063 targeted to PTEN at a dose of 0.5, 1.5, 5.0 and 15.0 mg/kg corresponding to 0.1, 0.32, 1.0 and 3.2 μmole/kg and with gapped oligomeric compounds 456694, 456696 and 396006 targeted to PTEN at a dose of 2.5, 7.9 and 25 mg/kg. The mice were sacrificed 48 hours following the last administration. Liver tissues were homogenized and mRNA levels were quantitated using real-time PCR using procedures illustrated herein for comparison to untreated control levels (% UTC). Plasma chemistry analysis was also completed. Tms were determined in 100 mM phosphate buffer, 0.1 mM EDTA, pH 7, at 260 nm using 4 μM of the gapped oligomeric compounds listed below and 4 μM of the complementary RNA.

| SEQ ID NO./ ISIS NO. | Composition (5' to 3') | Tm (° C.) vs. 14-mer RNA | Tm (° C.) vs. 20-mer RNA |
|---|---|---|---|
| 05/400844 | $C_{am}U_{am}$TAGCACTGGCC$_{am}U_{am}$ | 58.9 | 63.4 |
| 05/396006 | $C_{al}U_{al}$TAGCACTGGCC$_{al}U_{al}$ | 58.0 | 61.7 |
| 05/392745 | $C_{l}U_{l}$TAGCACTGGCC$_{l}U_{l}$ | 58.0 | 61.3 |
| 06/392063 | $^{Me}C_{l}T_{l}$TAGCACTGGC$^{Me}C_{l}T_{l}$ | 61.1 | 65.4 |
| 05/456694 | $C_{ah}U_{ah}$TAGCACTGGCC$_{ah}U_{ah}$ | 55.7 | 58.4 |
| 05/456696 | $C_{ag}U_{ag}$TAGCACTGGCC$_{ag}U_{ag}$ | 54.0 | 58.0 |

Each internucleoside linking group is a phosphorothioate and superscript Me indicates a 5-methyl group on the heterocyclic base (Bx). Subscripted nucleosides are defined below:

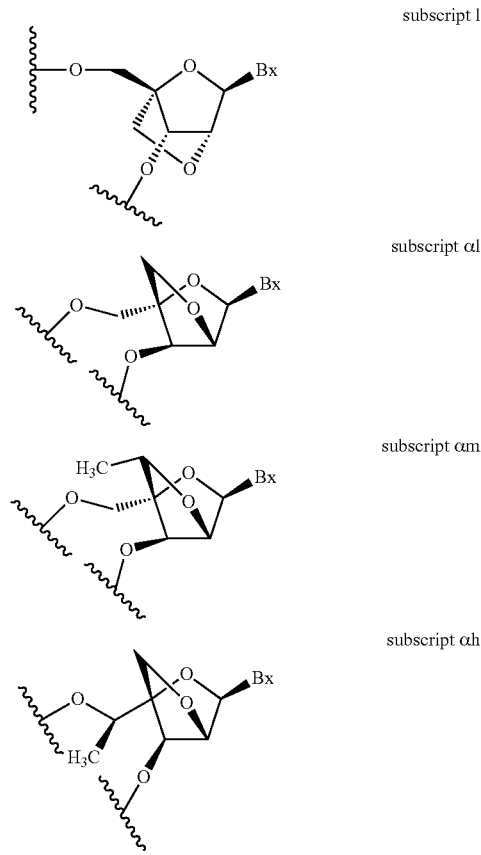

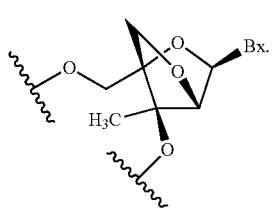

subscript αg

Estimated ED$_{50}$ concentrations for each gapped oligomeric compound were calculated using Graphpad Prism and the results are summarized below:

| SEQ ID NO./ ISIS NO. | ED$_{50}$ (μmol/kg) | ED$_{50}$ (mg/kg) |
|---|---|---|
| 06/392063 | 0.68 | 3.09 |
| 05/400844 | 1.08 | 4.92 |
| 05/396006 | 1.02 | 4.6 |
| 05/456694 | 1.49 | 6.8 |
| 05/456696 | 1.75 | 8.0 |

Liver transaminase levels, alanine aminotranferease (ALT) and aspartate aminotransferase (AST), in serum were also measured relative to saline injected mice. The approximate liver transaminase levels are listed in the table below.

| SEQ ID NO./ ISIS NO. | ALT @ 0.1 μmol/kg | ALT @ 0.32 μmol/kg | ALT @ 1 μmol/kg | ALT @ 3.2 μmol/kg |
|---|---|---|---|---|
| 06/392063 | 24 | 28 | 39 | 322 |
| 05/400844 | 28 | 27 | 24 | 26 |

ALT levels for compounds 396006, 400844, 456694 and 456696 were similar to that of the saline treated group

| SEQ ID NO./ ISIS NO. | Liver weight (% saline group) | Spleen weight (% saline group) |
|---|---|---|
| 06/392063 | 153 ± 10 | 116 ± 11 |
| 05/400844 | 149 ± 6 | 264 ± 50 |
| 05/396006 | 192 ± 13 | 172 ± 31 |
| 05/456694 | 136 ± 15 | 134 ± 8 |
| 05/456696 | 134 ± 5 | 203 ± 13 |

Example 28

| 12mer Tm study ||||
|---|---|---|---|
| SEQ ID NO. ISIS NO. | Composition (5' to 3') | Tm (° C.) | ΔTm/mod (° C.) |
| 07/449244 | GCGTTU$_{αj}$TTTGCT | 46.7 | +1.1 |
| 07/449245 | GCGTTU$_{αj}$T$_{αj}$TTGCT | 47.1 | +1.0 |
| 07/449246 | GCGTTU$_{αh}$TTTGCT | 49.0 | +3.4 |
| 07/449247 | GCGTTU$_{αh}$T$_{αh}$TTGCT | 53.7 | +4.1 |
| 07/454309 | GCGTTU$_{αg}$TTTGCT | 49.7 | +4.2 |
| 07/454310 | GCGTTU$_{αg}$T$_{αg}$TTGCT | 53.6 | +4.2 |
| 07/454307 | GCGTTU$_{αm}$TTTGCT | 51.3 | +5.5 |
| 07/454308 | GCGTTU$_{αm}$T$_{αm}$TTGCT | 55.2 | +4.8 |
| 07/438711 | GCGTTU$_{αl}$TTTGCT | 50.2 | +4.6 |
| 07/454306 | GCGTTU$_{αl}$T$_{αl}$TTGCT | 45.6 | +4.6 |
| 07/438704 | GCGTTUTTTGCT | 46.7 | +0.0 |

All internucleoside linkages are phosphodiester and all nucleosides not followed by a subscript are 2'-deoxyribonucleosides. The nucleosides followed by a subscript are defined below.

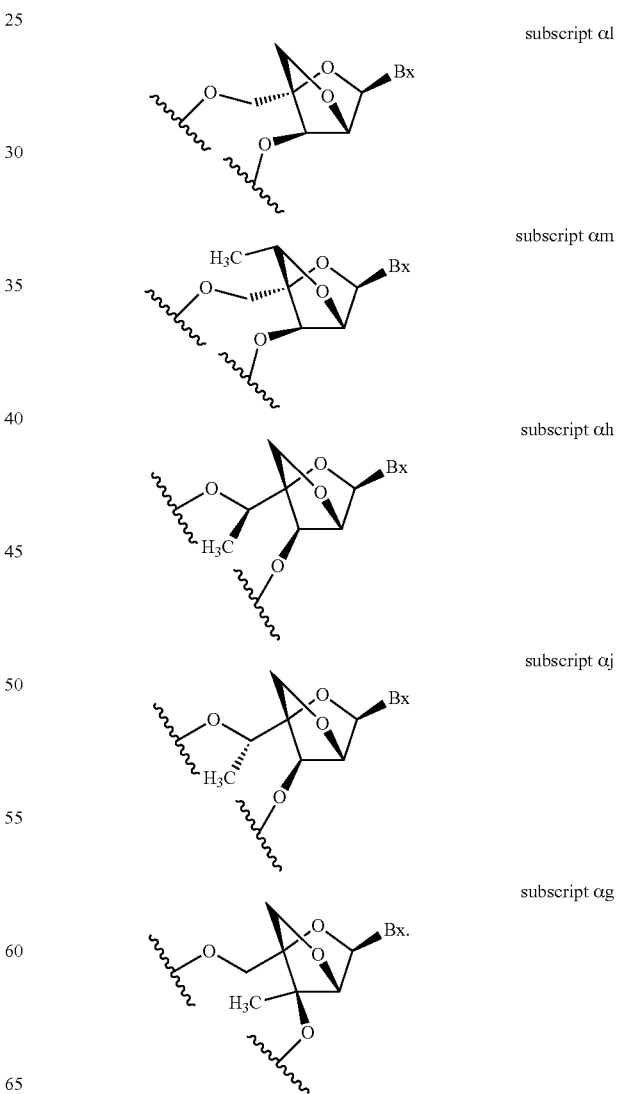

subscript αl subscript αm subscript αh subscript αj subscript αg

What is claimed is:

1. A bicyclic nucleoside having Formula I:

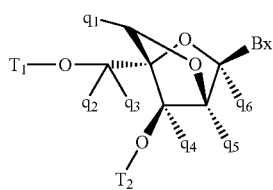

I wherein:
Bx is a heterocyclic base moiety;
one of $T_1$ and $T_2$ is H or a hydroxyl protecting group and the other of $T_1$ and $T_2$ is H, a hydroxyl protecting group or a reactive phosphorus group;
$q_1$, $q_2$, $q_3$, $q_4$, $q_5$ and $q_6$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;
wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and
wherein at least one of $q_1$, $q_2$, $q_3$, $q_4$, $q_5$ and $q_6$ is other than H.

2. The bicyclic nucleoside of claim 1 wherein at least one of $q_1$, $q_2$, $q_3$, $q_4$, $q_5$ and $q_6$ is $C_1$-$C_6$ alkyl or substituted $C_1$-$C_6$ alkyl.

3. The bicyclic nucleoside of claim 1 wherein at least one of $q_1$, $q_2$, $q_3$, $q_4$, $q_5$ and $q_6$ is substituted $C_1$-$C_6$ alkyl having at least one substituent group selected from fluoro and $OCH_3$.

4. The bicyclic nucleoside of claim 1 wherein at least one of $q_1$, $q_2$, $q_3$, $q_4$, $q_5$ and $q_6$ is methyl.

5. The bicyclic nucleoside of claim 1 having Formula II:

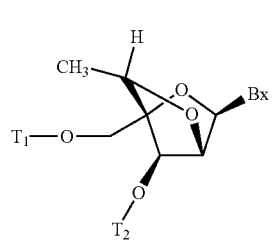

II wherein:

Bx is a heterocyclic base moiety; and one of $T_1$ and $T_2$ is H or a hydroxyl protecting group and the other of $T_1$ and $T_2$ is H, a hydroxyl protecting group or a reactive phosphorus group.

6. The bicyclic nucleoside of claim 1 having Formula III:

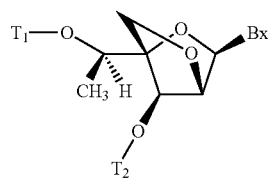

III wherein:

Bx is a heterocyclic base moiety; and one of $T_1$ and $T_2$ is H or a hydroxyl protecting group and the other of $T_1$ and $T_2$ is H, a hydroxyl protecting group or a reactive phosphorus group.

7. The bicyclic nucleoside of claim 1 having Formula IV:

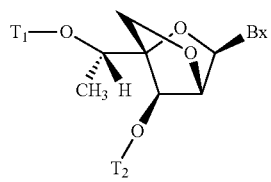

IV wherein:

Bx is a heterocyclic base moiety; and one of $T_1$ and $T_2$ is H or a hydroxyl protecting group and the other of $T_1$ and $T_2$ is H, a hydroxyl protecting group or a reactive phosphorus group.

8. The bicyclic nucleoside of claim 1 having Formula IX:

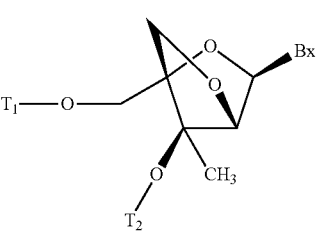

IX wherein:

Bx is a heterocyclic base moiety; and one of $T_1$ and $T_2$ is H or a hydroxyl protecting group and the other of $T_1$ and $T_2$ is H, a hydroxyl protecting group or a reactive phosphorus group.

9. The bicyclic nucleoside of claim 1 wherein $T_1$ is 4,4'-dimethoxytrityl and $T_2$ is diisopropylcyanoethoxy phosphoramidite.

10. An oligomeric compound comprising at least one bicyclic nucleoside having Formula V:

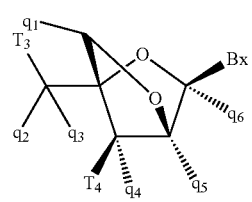

V wherein independently for each bicyclic nucleoside having Formula V:

Bx is a heterocyclic base moiety;

$T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound;

$q_1$, $q_2$, $q_3$, $q_4$, $q_5$ and $q_6$ are each, independently, H, $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl or substituted $C_2$-$C_6$ alkynyl;

wherein each substituted group is, independently, mono or poly substituted with optionally protected substituent groups independently selected from halogen, oxo, $OJ_1$, $NJ_1J_2$, $SJ_1$, $N_3$, $OC(=O)J_1$ and CN, wherein each $J_1$ and $J_2$ is, independently, H or $C_1$-$C_6$ alkyl; and wherein at least one of $q_1$, $q_2$, $q_3$, $q_4$, $q_5$ and $q_6$ is other than H.

11. The oligomeric compound of claim 10 wherein at least one of $q_1$, $q_2$, $q_3$, $q_4$, $q_5$ and $q_6$ is $C_1$-$C_6$ alkyl or substituted $C_1$-$C_6$ alkyl for at least one of said bicyclic nucleoside of Formula V.

12. The oligomeric compound of claim 11 wherein each substituted $C_1$-$C_6$ alkyl comprises at least one substituent group selected from fluoro and $OCH_3$.

13. The oligomeric compound of claim 10 wherein at least one of $q_1$, $q_2$, $q_3$, $q_4$, $q_5$ and $q_6$ is methyl for at least one of said bicyclic nucleoside of Formula V.

14. The oligomeric compound of claim 10 wherein at least one of said bicyclic nucleoside has Formula VI:

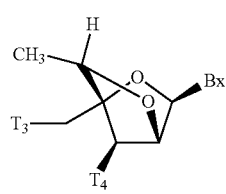

VI wherein:

Bx is a heterocyclic base moiety; and $T_3$ and $T_4$ are each, independently, hydroxyl, a protected hydroxyl, a linked conjugate group or an internucleoside linking group attaching the bicyclic nucleoside to the oligomeric compound wherein at least one of $T_3$ and $T_4$ is an internucleoside linking group attaching the bicyclic nucleoside to the oligomeric compound.

15. The oligomeric compound of claim 10 wherein at least one of said bicyclic nucleoside has Formula VII:

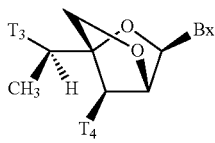

VII wherein:
Bx is a heterocyclic base moiety; and
T$_3$ and T$_4$ are each, independently, hydroxyl, a protected hydroxyl, a linked conjugate group or an internucleoside linking group attaching the bicyclic nucleoside to the oligomeric compound wherein at least one of T$_3$ and T$_4$ is an internucleoside linking group attaching the bicyclic nucleoside to the oligomeric compound.

16. The oligomeric compound of claim 10 wherein at least one of said bicyclic nucleoside has Formula VIII:

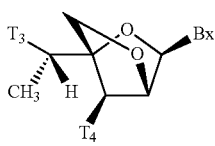

VIII wherein:
Bx is a heterocyclic base moiety; and
T$_3$ and T$_4$ are each, independently, hydroxyl, a protected hydroxyl, a linked conjugate group or an internucleoside linking group attaching the bicyclic nucleoside to the oligomeric compound wherein at least one of T$_3$ and T$_4$ is an internucleoside linking group attaching the bicyclic nucleoside to the oligomeric compound.

17. The oligomeric compound of claim 10 wherein at least one of said bicyclic nucleoside has Formula X:

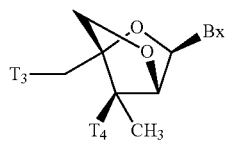

X wherein:
Bx is a heterocyclic base moiety; and
T$_3$ and T$_4$ are each, independently, hydroxyl, a protected hydroxyl, a linked conjugate group or an internucleoside linking group attaching the bicyclic nucleoside to the oligomeric compound wherein at least one of T$_3$ and T$_4$ is an internucleoside linking group attaching the bicyclic nucleoside to the oligomeric compound.

18. The oligomeric compound of claim 10 wherein each internucleoside linking group is, independently, selected from phosphodiester or phosphorothioate.

19. The oligomeric compound of claim 10 wherein each internucleoside linking group is a phosphorothioate.

20. The oligomeric compound of claim 10 comprising at least one region of at least two contiguous bicyclic nucleosides having Formula V.

21. The oligomeric compound of claim 20 further comprising at least one region of from 8 to 14 contiguous β-D-2'-deoxyribofuranosyl nucleosides.

22. The oligomeric compound of claim 20 further comprising at least one region of from 9 to 12 contiguous β-D-2'-deoxyribofuranosyl nucleosides.

23. The oligomeric compound of claim 10 comprising one region of from 2 to three contiguous bicyclic nucleosides having Formula V, an optional second region of 1 or 2 contiguous bicyclic nucleosides having Formula V and a third region of from 8 to 14 β-D-2'-deoxyribofuranosyl nucleosides wherein said third region is located between said first and said second regions.

24. The oligomeric compound of claim 10 comprising from 8 to 40 monomer subunits.

25. The oligomeric compound of claim 10 wherein q$_1$, q$_2$, q$_3$, q$_4$, q$_5$ and q$_6$ are uniformly modified for each of said at least one bicyclic nucleoside having Formula V.

26. A method of inhibiting gene expression comprising contacting one or more cells, a tissue or an animal with an oligomeric compound of claim 10 wherein said oligomeric compound is complementary to a target RNA.

27. The method of claim 26 wherein said cells are in a human.

28. The method of claim 26 wherein said target RNA is selected from mRNA, pre-mRNA and micro RNA.

29. The method of claim 28 wherein said target RNA is mRNA.

30. The method of claim 28 wherein said target RNA is human mRNA.

31. The method of claim 26 wherein said target RNA is cleaved thereby inhibiting its function.

32. The method of claim 26 further comprising detecting the levels of target RNA.

* * * * *

SEQUENCE LISTING

<160> NUMBER OF SEQ ID NOS: 7

<210> SEQ ID NO 1
<211> LENGTH: 3160
<212> TYPE: DNA
<213> ORGANISM: H. sapiens

<400> SEQUENCE: 1

| | | | | | |
|---|---|---|---|---|---|
| cctcccctcg | cccggcgcgg | tcccgtccgc | ctctcgctcg | cctcccgcct | ccctcggtc | 60 |
| ttccgaggcg | cccgggctcc | cggcgcggcg | gcggaggggg | cgggcaggcc | ggcgggcggt | 120 |
| gatgtggcag | gactctttat | gcgctgcggc | aggatacgcg | ctcggcgctg | ggacgcgact | 180 |
| gcgctcagtt | ctctcctctc | ggaagctgca | gccatgatgg | aagtttgaga | gttgagccgc | 240 |
| tgtgaggcga | ggccgggctc | aggcgaggga | gatgagagac | ggcggcggcc | gcggcccgga | 300 |
| gcccctctca | gcgcctgtga | gcagccgcgg | gggcagcgcc | ctcggggagc | cggccggcct | 360 |
| gcggcggcgg | cagcggcggc | gtttctcgcc | tcctcttcgt | cttttctaac | cgtgcagcct | 420 |
| cttcctcggc | ttctcctgaa | agggaaggtg | gaagccgtgg | gctcgggcgg | gagccggctg | 480 |
| aggcgcggcg | gcggcggcgg | cggcacctcc | cgctcctgga | gcgggggga | gaagcggcgg | 540 |
| cggcggcggc | cgcggcggct | gcagctccag | ggagggggtc | tgagtcgcct | gtcaccattt | 600 |
| ccagggctgg | gaacgccgga | gagttggtct | ctccccttct | actgcctcca | acacggcggc | 660 |
| ggcggcggcg | gcacatccag | ggacccgggc | cggttttaaa | cctcccgtcc | gccgccgccg | 720 |
| cacccccgt | ggcccgggct | ccggaggccg | ccggcggagg | cagccgttcg | gaggattatt | 780 |
| cgtcttctcc | ccattccgct | gccgccgctg | ccaggcctct | ggctgctgag | gagaagcagg | 840 |
| cccagtcgct | gcaaccatcc | agcagccgcc | gcagcagcca | ttaccggct | gcggtccaga | 900 |
| gccaagcggc | ggcagagcga | ggggcatcag | ctaccgccaa | gtccagagcc | atttccatcc | 960 |
| tgcagaagaa | gccccgccac | cagcagcttc | tgccatctct | ctcctccttt | tcttcagcc | 1020 |
| acaggctccc | agacatgaca | gccatcatca | aagagatcgt | tagcagaaac | aaaaggagat | 1080 |
| atcaagagga | tggattcgac | ttagacttga | cctatattta | tccaaacatt | attgctatgg | 1140 |
| gatttcctgc | agaaagactt | gaaggcgtat | acaggaacaa | tattgatgat | gtagtaaggt | 1200 |
| ttttggattc | aaagcataaa | aaccattaca | agatatacaa | tctttgtgct | gaaagacatt | 1260 |
| atgacaccgc | caaatttaat | tgcagagttg | cacaatatcc | ttttgaagac | cataacccac | 1320 |
| cacagctaga | acttatcaaa | cccttttgtg | aagatcttga | ccaatggcta | agtgaagatg | 1380 |
| acaatcatgt | tgcagcaatt | cactgtaaag | ctggaaaggg | acgaactggt | gtaatgatat | 1440 |
| gtgcatattt | attacatcgg | ggcaaatttt | taaaggcaca | agaggcccta | gatttctatg | 1500 |
| gggaagtaag | gaccagagac | aaaaagggag | taactattcc | cagtcagagg | cgctatgtgt | 1560 |
| attattatag | ctacctgtta | aagaatcatc | tggattatag | accagtggca | ctgttgtttc | 1620 |
| acaagatgat | gtttgaaact | attccaatgt | tcagtggcgg | aacttgcaat | cctcagtttg | 1680 |
| tggtctgcca | gctaaaggtg | aagatatatt | cctccaattc | aggacccaca | cgacgggaag | 1740 |
| acaagttcat | gtactttgag | ttccctcagc | cgttacctgt | gtgtggtgat | atcaaagtag | 1800 |

```
agttcttcca caaacagaac aagatgctaa aaaaggacaa atgtttcac ttttgggtaa    1860 atacattctt cataccagga ccagaggaaa cctcagaaaa agtagaaaat ggaagtctat   1920
gtgatcaaga aatcgatagc atttgcagta tagagcgtgc agataatgac aaggaatatc   1980
tagtacttac tttaacaaaa aatgatcttg acaaagcaaa taaagacaaa gccaaccgat   2040
acttttctcc aaattttaag gtgaagctgt acttcacaaa aacagtagag agccgtcaa    2100 atccagaggc tagcagttca acttctgtaa caccagatgt tagtgacaat gaacctgatc   2160
attatagata ttctgacacc actgactctg atccagagaa tgaaccttttt gatgaagatc  2220 agcatacaca aattacaaaa gtctgaattt ttttttatca agagggataa acaccatga    2280 aaataaactt gaataaactg aaaatggacc ttttttttttt taatggcaat aggacattgt   2340
gtcagattac cagttatagg aacaattctc ttttcctgac caatcttgtt ttaccctata    2400
catccacagg gttttgacac ttgttgtcca gttgaaaaaa ggttgtgtag ctgtgtcatg    2460 tatataccctt tttgtgtcaa aaggacattt aaaattcaat taggattaat aaagatggca   2520 cttttcccgtt ttattccagt tttataaaaa gtggagacag actgatgtgt atacgtagga   2580 atttttttcct tttgtgttct gtcaccaact gaagtggcta aagagctttg tgatatactg    2640
gttcacatcc taccccttttg cacttgtggc aacagataag tttgcagttg gctaagagag    2700 gttttccgaaa ggttttgcta ccattctaat gcatgtattc gggttagggc aatggaggggg    2760 aatgctcaga aaggaaataa ttttatgctg gactctggac catataccat ctccagctat     2820
ttacacacac ctttctttag catgctacag ttattaatct ggacattcga ggaattggcc     2880
gctgtcactg cttgttgttt gcgcatttttt ttttaaagca tattggtgct agaaaaggca     2940
gctaaaggaa gtgaatctgt attggggtac aggaatgaac cttctgcaac atcttaagat     3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                           3160

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
aatggctaag tgaagatgac aatcat                                         26

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
tgcacatatc attacaccag ttcgt                                          25

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4
```

-continued

```
ttgcagcaat tcactgtaaa gctggaaagg                                      30

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: bases at these positions are RNA

<400> SEQUENCE: 5
cutagcactg gccu                                                       14

<210> SEQ ID NO 6
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 6
cttagcactg gcct                                                       14

<210> SEQ ID NO 7
<211> LENGTH: 12
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 6
<223> OTHER INFORMATION: bases at these positions are RNA

<400> SEQUENCE: 7
gcgttutttg ct                                                         12
```